United States Patent [19]
Hoenes et al.

[11] Patent Number: 5,484,708
[45] Date of Patent: Jan. 16, 1996

[54] METHOD FOR THE COLORIMETRIC DETERMINATION OF AN ANALYTE WITH A PQQ-DEPENDENT DEHYDROGENASE

[75] Inventors: Joachim Hoenes, Zwingenberg; Volker Unkrig, Ladenburg, both of Germany

[73] Assignee: Boehringer Mannheim GmbH, Mannheim, Germany

[21] Appl. No.: 224,869

[22] Filed: Apr. 8, 1994

[30] Foreign Application Priority Data

Apr. 8, 1993 [DE] Germany .......................... 43 11 464.4

[51] Int. Cl.$^6$ .............................. C12Q 1/54; C12Q 1/00; C12P 17/18; G01N 33/48
[52] U.S. Cl. .................. 435/14; 435/4; 435/26; 435/25; 435/118; 435/119; 435/120; 435/28; 435/133; 436/63
[58] Field of Search .................... 435/14, 4, 26, 435/25, 118, 119, 120, 133, 28; 436/63

[56] References Cited

U.S. PATENT DOCUMENTS

| | | | |
|---|---|---|---|
| 4,746,607 | 5/1988 | Mura et al. | 435/25 |
| 4,828,983 | 5/1989 | McClune | 435/14 |
| 4,879,243 | 11/1989 | Mura et al. | 436/63 |
| 4,994,382 | 2/1991 | Ameyama et al. | 435/133 |
| 5,122,244 | 6/1992 | Hoenes et al. | 204/153.12 |
| 5,206,147 | 4/1993 | Hoenes | 435/25 |
| 5,234,818 | 8/1993 | Zimmermann et al. | 435/28 |
| 5,240,860 | 3/1993 | Hoenes et al. | 436/111 |
| 5,334,508 | 8/1994 | Hoenes | 435/25 |

FOREIGN PATENT DOCUMENTS

| | | |
|---|---|---|
| 0354441 | 8/1989 | European Pat. Off. |
| 0441222A2 | 1/1991 | European Pat. Off. |
| 2147466 | 9/1971 | Germany. |
| WO-A-92 07953 | 10/1991 | WIPO. |
| 92/07953 | 5/1992 | WIPO. |

OTHER PUBLICATIONS

Chemical Abstracts, vol. 117, No. 1, (1992), #3829x.
Adachi et al., *Enzymatic Determination of Pyrroloquinoline Quinone with a Quinoprotein Glycerol Dehydrogenase*, Agric. Biol. Chem., 52 (8), 2081–2, 1988.

*Primary Examiner*—Michael G. Wityshyn
*Assistant Examiner*—Louise N. Leary
*Attorney, Agent, or Firm*—Nikaido, Marmelstein, Murray & Oram

[57] ABSTRACT

The invention concerns a method for the colorimetric determination of an analyte by means of enzymatic oxidation with a PQQ-dependent dehydrogenase in the presence of an electron acceptor from the group of the electron-rich aromatic nitroso compounds by enzymatic reduction of the nitroso compound to an imino compound and detection of the imino compound by color formation. In addition the invention concerns a corresponding agent containing a PQQ-dependent dehydrogenase, an electon-rich aromatic nitroso compound as well as, if desired, a detection reagent for imino compounds. The invention in addition concerns novel nitrosoamino compounds which form colored quinone diimines on reduction as well as their use for the colorimetric enzymatic determination of an analyte.

32 Claims, 4 Drawing Sheets

METHOD FOR THE COLORIMETRIC DETERMINATION OF AN ANALYTE WITH A PQQ-DEPENDENT DEHYDROGENASE

The invention concerns a method for the colorimetric determination of an analyte by means of enzymatic oxidation with a pyrrolo-quinoline quinone (PQQ)-dependent dehydrogenase in the presence of an electron acceptor from the group of electron-rich aromatic nitroso compounds and determination of the reduced electron acceptor by formation of colour as a measure of the amount of analyte. In addition the invention concerns an agent for the colorimetric determination of an analyte by enzymatic oxidation containing a PQQ-dependent dehydrogenase, an electron-rich aromatic nitroso compound as well as a colour forming non-oxidative detection reagent for the imino compound which forms on reduction from the electron-rich aromatic nitroso compound. The invention in addition concerns novel nitrosoaniline compounds, their production as well as their use for the colorimetric enzymatic determination of an analyte.

In analytics, enzymatic oxidations enable the detection and determination of substances in various sample materials. In this case an oxidizing enzyme acts on an appropriate enzyme substrate in the presence of an acceptor which receives the electrons of the oxidation reaction. The reduction of the electron acceptor indicates the presence of the enzyme substrate. In this connection it has previously proven to be particularly advantageous when the reduced electron acceptor can be detected by colour formation since this is not necessarily only possible by means of expensive measuring devices but can also be carried out visually if desired.

Known methods for the colorimetric determination of substances by means of enzymes with an oxidizing action use oxidases or dehydrogenases. Both enzyme groups belong to the main group of oxidoreductases ("Römpps Chemielexikon, Francksche Verlagsbuchhandlung, Stuttgart", 8th Ed. 1985, Vol. 4, page 2952; "Lexikon Biochemie, Publisher H. D. Jakubke, "Verlag Chemie, Weinheim" 2nd Edition, 1981, page 194), whose members can be differentiated according to their natural electron acceptors.

The natural electron acceptor for oxidases is molecular oxygen ("Römpps Chemielexikon, Francksche Verlagsbuchhandlung" Stuttgart, 8th Edition, 1985, 4th Volume, page 2946). In analyte determinations the analyte is oxidized by an oxidase and $O_2$ in this process. The $H_2O_2$ which forms is used to oxidize a leuco dye with the aid of peroxidase. A. Kunst et al. in Methods in enzymatic analysis, Publ. H. U. Bergmeyer, "Verlag Chemie, Weinheim," 3rd Edition, 1984, Volume 6, page 178–185, is cited as being representative for the state of the art in the use of oxidases for the colorimetric determination of analytes. In this reference glucose is detected in serum, plasma or in deproteinized blood by reaction with glucose oxidase and atmospheric oxygen in aqueous solution in that the hydrogen peroxide formed in this reaction by the reduction of oxygen is reduced in the presence of peroxidase and thereby acts on phenol and 4-aminophenazone which are also present in the reaction mixture to form a colour. The high redox potential of $H_2O_2$ and the non-selectivity and instability of peroxidase often lead to limitations of such tests. For example transition metal ions or haem or haem proteins, such as those which can easily occur in samples derived from blood, interfere because they decompose hydrogen peroxide. Sample constituents such as bilirubin and drugs such as methyldopa which can indeed occur in samples derived from blood or in urine can lead to colour formation with hydrogen peroxide and peroxidase and thus to false results; they can also reduce and thus bleach dye which has already formed.

The oxygen requirement of the oxidases has also proven to be an additional disadvantage in particular when carrying out the aforementioned method of determination on solid carriers, in so-called dry tests. The diffusion of oxygen from the air into the reaction medium can become the rate-determining step especially in situations where much oxygen is needed to oxidize high concentrations of enzyme substrate and this leads to long reaction times or to false results especially in kinetic methods of determination.

Dehydrogenases can in general be divided into those which require nicotinamide adenine dinucleotide (NAD) or nicotinamide adenine dinucleotide phosphate (NADP) as the natural direct electron acceptor for the oxidation of enzyme substrates and into those which are non-NAD-dependent or non-NADP-dependent and thus use other substances as natural direct electron acceptors in enzymatic oxidation reactions. In particular the PQQ-dependent and flavine-dependent dehydrogenases are part of the group of non-NAD-dependent or non-NADP-dependent dehydrogenases.

The use of NAD-dependent dehydrogenases for colorimetric measurements is known for example from DE-A-2147466. This application describes that lactate dehydrogenase catalyses the conversion of lactate and nicotinamide-adenine dinucleotide into pyruvate and reduced nicotinamide adenine dinucleotide. The NADH which is formed then for example reacts with tetrazolium salts in the presence of the enzyme diaphorase to form NAD and coloured formazans whose concentration can be determined photometrically. N-Methylphenazinium methosulfate is also mentioned instead of diaphorase as a reduction catalyst for the transfer of electrons from NADH onto the tetrazolium salt.

Disadvantages of this method can be seen in the fact that in addition to NADH, other substances with a reducing action such as glutathione or drugs such as methyldopa or dobesylate which may occur in biological samples such as for example blood, serum, plasma or urine also convert tetrazolium salts into corresponding formazans in the presence of unspecific reduction catalysts such as diaphorase or N-methylphenazinium methosulfate and thus lead to false-positive results although they would not react as rapidly with tetrazolium salts in the absence of reduction catalysts.

The oxidative, enzymatic detection of analytes by means of flavine-dependent oxidases or non-NAD-dependent dehydrogenases such as PQQ-dependent dehydrogenases using electron-rich aromatic nitroso compounds is known from U.S. Pat. No. 5,206,147. In this method of detection, the aromatic nitroso compound is reduced enzymatically to a corresponding electron-rich, aromatic amine which is either detected by heteropolyblue formation using a precipitated, poorly soluble heteropoly acid or is coupled with a coupling reagent in the presence of an oxidizing agent to form a dye. However, the blue-grey colour gradations of the heteropolyblue formation are not very suitable for an exact visual evaluation. A disadvantage of the colorimetric detection of the aromatic amines which are usually not coloured or only very weakly coloured using a chromogenic coupling reagent is that an oxidizing agent is additionally required. Since such an oxidizing agent would interfere with the enzymatic reduction of the aromatic nitroso compound to the aromatic amine, the detection reaction has to be carried out in two separate steps: in the first step the aromatic nitroso compound is reduced enzymatically to an aromatic amine and in a second separate step an oxidizing agent is added for the oxidative coupling of the aromatic amine with a chromogenic coupling reagent.

A further disadvantage of this method of detection is that two equivalents of the analyte have to be oxidized for the reduction of each equivalent of an aromatic nitroso compound to an aromatic amine. This can lead to an unsatisfactory sensitivity of such a detection method, in particular at low analyte concentrations.

The object of the present invention was therefore to eliminate the aforementioned disadvantages of the prior art and to provide a more simple, more sensitive method and agent for the oxidative detection of analytes which is less susceptible to interference and can be optically evaluated in an improved manner, which in particular can be carried out in one step and yields colours which can be readily evaluated by visual means over the entire visible wavelength range.

The object is achieved by the invention as it is characterized in the claims.

Accordingly a method for the colorimetric determination of an analyte by means of enzymatic oxidation of the analyte with an oxidoreductase in the presence of a direct electron acceptor from the group of the electron-rich aromatic nitroso compounds was found in which the reduced electron acceptor is determined by colour formation as a measure of the amount of analyte which is characterized in that the electron-rich aromatic nitroso compound is reduced to an imino compound with concomitant oxidation of the analyte in the presence of a PQQ-dependent dehydrogenase and this imino compound is detected by colour formation without further enzymatic reduction to form an aromatic amine.

The invention in particular concerns a method for the colorimetric determination of an analyte with an oxidoreductase in the presence of a direct electron acceptor from the group of the electron-rich aromatic nitroso compounds in which the reduced electron acceptor is determined by colour formation as a measure of the amount of analyte, which is characterized in that the electron-rich aromatic nitroso compound is reduced to form an imino compound with concomitant oxidation of the analyte in the presence of a PQQ-dependent dehydrogenase and this imino compound is determined colorimetrically by reaction with a chromogenic non-oxidative detection reaction instead of being enzymatically reduced further to an aromatic amine.

In addition an agent was found for the colorimetric determination of an analyte by enzymatic oxidation of the analyte containing a PQQ-dependent dehydrogenase and a direct electron acceptor from the group of electron-rich aromatic nitroso compounds which is characterized in that it either contains an electron-rich aromatic nitroso compound which forms a coloured imino compound on enzymatic reduction or that it in addition contains a chromogenic non-oxidative detection reagent for the imino compound that is formed by reduction of the electron-rich nitroso compound.

According to the invention "analyte" is understood as a substance which is oxidized enzymatically. In many cases the analyte is that substance which is intended to be directly detected or quantitatively determined in the sample to be examined. For example glucose can be directly oxidized with PQQ-dependent glucose dehydrogenase (glucose dye oxidoreductase) and colorimetrically determined. However, it is also possible that the analyte is firstly formed from another substance by one or several preceding reactions so that the concentration of the initial substance can be implied indirectly from the colorimetric determination of the analyte.

The analyte in the present invention is that substance which is accepted as the substrate for the PQQ-dependent dehydrogenase that is used.

PQQ-dependent dehydrogenases contain pyrroloquinoline quinone as a cofactor. A review of such "quinoproteins" is given by J. A. Jongejahn et al. in "PQQ and Quinoproteins" Kluver Academic Publ. Dordrecht, Netherlands 1989. Examples of enzymes that can be used according to the invention are PQQ-dependent glucose dehydrogenase (glucose dye oxidoreductase, E. C. 1.1.1.50/1.1.1.91/1.1.1.97), alcohol dehydrogenase or lactate dehydrogenase. In the method according to the invention the PQQ-dependent glucose dehydrogenase in particular can be used advantageously for the colorimetric determination of glucose.

Electron-rich aromatic nitroso compounds are used as direct electron acceptors which accept the electrons from the enzyme/cofactor system dehydrogenase/PQQ such as those which are known as electron acceptors for oxidases and non-NADH-dependent dehydrogenases from U.S. Pat. No. 5,206,147 and U.S. Pat. No. 5,122,244 and in which a nitroso group is bound directly to an electron-rich aromatic nucleus. "Direct" electron acceptors means that under enzyme catalysis the electrons are accepted directly from the enzyme/cofactor system without the necessity for a reduction catalyst.

Reducible electron-rich, aromatic nitroso compounds which can be used within the sense of the present invention are compounds which accept the electrons from the enzyme which are formed during the oxidation of the appropriate substrate for the PQQ-dependent dehydrogenase used and form imino compounds in this process. A corresponding imino compound contains an imino group = NH that is bound via its double bond to the formerly aromatic nucleus and is conjugated with its double bond electrons. Electron-rich aromatic nitroso compounds contain one or several electron-donating residues or groups on or in the aromatic nucleus which promote formation of an imino compound by becoming conjugated by means of electron release with the imino group via the formerly aromatic nucleus.

These are on the one hand substituents which exert a +M effect on the aromatic nucleus.

reduction e.g. R—Ar—NO→ R'= Ar'= NH

Examples of residues R with a +M effect bound to an aromatic nucleus are substituents such as hydroxy, alkoxy, aryloxy, alkylthio, arylthio, amino, monoalkylamino, monoarylamino, dialkylamino and diarylamino residues.

In the case of nitrosobenzene derivatives, these substituents for example show their effect especially when they are placed in the ortho and/or in the para position in relation to the nitroso group.

Groups with an electron-donating and imine structure-promoting effect can also be a component of a heteroaromatic ring system.

Examples are heterocyclic aromatic nitroso compounds with an excess of $\pi$-electrons in which the aromatic ring system is so rich in electrons that an external +M substituent is not necessary for the formation of a mesomerically stabilized imine group after the reduction. The excess of $\pi$-electrons is a result of the fact that more aromatic $\pi$-electrons are present than there are ring atoms over which the $\pi$-electrons can be distributed. Such heterocycles are known to a person skilled in the art.

Examples of such aromatic heterocycles are antipyrine, pyrazolo heterocycles and pyrazoles.

The richness in electrons of the electron-rich aromatic nitroso compounds used according to the invention has the additional effect that these nitroso compounds are to a certain extent in equilibrium with the equivalent oxime resonance structure by means of keto-enol tautomerism.

$$R-Ar-N=O \rightleftharpoons R'=Ar'=N-OH$$

Within the scope of the invention it is intended to encompass both resonance structures of the tautomerism by the term "aromatic nitroso compounds" as substances which can be used according to the invention.

In the case of the aforementioned +M substituents alkoxy, alkylthio, monoalkylamino and dialkylamino residues are residues in which alkyl represents a hydrocarbon residue with 1 to 6 carbon atoms which in turn can be substituted by a hydroxy group, an amino group substituted if desired once or several times by alkyl with 1 to 6 carbon atoms, $PO_3H_2$, $SO_3H$ or $CO_2H$. The acid residues $PO_3H_2$, $SO_3H$ and $CO_2H$ can be present as such or in a salt form as ammonium, alkali or alkaline earth salts.

Aryloxy and arylthio residues contain aromatic residues with 6 to 10 carbon atoms wherein phenoxy and phenylthio residues are particularly preferred.

Ammonium salts are those which contain the ammonium ion $NH_4^+$ or those which contain ammonium cations that are substituted once or several times by alkyl, aryl or aralkyl residues. Alkyl in alkyl and aralkyl residues denotes a hydrocarbon residue with 1 to 6 carbon atoms. Aryl in aryl and aralkyl residues is an aromatic ring system with 6 to 10 carbon atoms wherein phenyl is preferred. A preferred aralkyl residue is benzyl.

Alkali salts are preferably those of lithium, sodium or potassium. Alkaline earth salts are preferably those of magnesium or calcium.

The examples of +M substituents given above are not to be understood as a complete list. A person skilled in the art will know in an individual case whether a given residue R is a +M substituent and at which position it exerts this effect on an aromatic system, or which aromatic heterocycles contain such a corresponding group in the ring system and in this respect all these residues should be possible substituents in aromatic nitroso compounds which can be used according to the invention.

The basic aromatic framework of the aromatic nitroso compound to be used preferably represents an electron-rich aromatic ring of 5–7 and particularly preferably of 5–6 carbon or heteroatoms which can be anellated with one or two aromatic or/and alicyclic rings. In this case aromatic carbon systems as well as heteroaromatic systems each with 5–7 and preferably with 5–6 carbon or heteroatoms come into consideration for the aromatic anellated rings.

Alicyclic rings are understood as saturated or unsaturated cycloaliphatics with 5–7 carbon atoms or heteroatoms, preferably 5 or 6 carbon atoms. Heteroatoms are understood as nitrogen, oxygen or sulphur.

Preferred nitroso compounds which can be used according to the invention are nitrosobenzene derivatives.

Nitrosobenzene derivatives are also understood to include nitrosobenzene which is anellated with one or several aromatic or/and alicyclic rings. In this case aromatic carbon systems as well as heteroaromatics each with 5–7 and preferably with 5 or 6 ring atoms come into consideration as aromatic rings. Examples are anellated benzene or naphthalene rings or an anellated pyridine ring.

Nitrosobenzene derivatives of the general formula I are particularly preferred

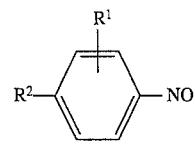

in which $R^1$
denotes hydrogen, hydroxy, alkyl substituted if desired by hydroxy, COOH, $PO_3H_2$, or $SO_3H$, alkoxy, alkylthio, aryloxy, arylthio, halogen, or amino which is substituted if desired once or several times by alkyl which is substituted if desired by hydroxy, $PO_3H_2$, dialkylphosphinyl, $SO_3H$ or $CO_2H$,
and $R^2$
denotes a hydroxy group, alkoxy, aryloxy, arylthio or alkylthio group in which the alkyl residue is in turn substituted if desired by a hydroxy group, an alkoxy group, an amino group which is substituted if desired once or several times by alkyl, $PO_3H_2$, $SO_3H$ or $CO_2H$ as such or in the form of a salt as ammonium, alkali or alkaline earth salts or it denotes an amino group $NR^3R^4$,
in which $R^3$ and $R^4$ can be the same or different and denote hydrogen, an aryl or alkyl group which can be in turn substituted by a hydroxy, alkoxy, hydroxyalkoxy or polyalkoxy group which is substituted by hydroxy if desired, $PO_3H_2$, $SO_3H$, COOH as such or in the form of a salt or denote an amino group which can be substituted once or several times by alkyl, or in which $R^3$ and $R^4$ can represent an alkylene residue which is interrupted if desired by oxygen, sulphur or nitrogen wherein nitrogen is substituted by an alkyl, hydroxyalkyl, hydroxyalkoxy-alkyl, alkoxyhydroxyalkyl, alkoxycarbonyl-alkyl, dioxanylylalkyl or polyalkoxyalkyl residue and the alkyl moiety of each of these can if desired in turn be substituted by a hydroxy residue, or if $R^1$ is in the ortho position in relation to $NR^3R^4$, $R^3$ or $R^4$ also together with $R^1$ can represent an alkylene residue.

In this case halogen denotes fluorine, chlorine, bromine or iodine. Fluorine and chlorine are particularly preferred.

Alkyl in alkyl, alkoxy or alkylthio denotes a hydrocarbon residue with 1–6 carbon atoms, residues with 1–3 carbon atoms are particularly preferred. The aforementioned definition for alkyl also applies to the alkyl moiety in hydroxyalkyl, dialkylaminoalkyl, hydroxyalkoxyalkyl, alkoxyalkyl, polyalkoxyalkyl, alkoxyhydroxyalkyl and dioxanylyl-alkyl residues. A dioxanylyl-alkyl residue is a residue in which a dioxane ring system is bound to an alkyl residue. It is preferably a 1,4-dioxane ring system, i.e.

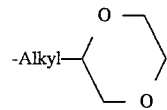

A polyalkoxyalkyl residue is a —alkyl—(alkoxy)$_n$—alkoxy residue
in which n equals 1–10. Preferably n equals 1–4. Particularly preferably n equals 1–3. An alkylene residue is a straight-chained or branched—preferably straight-chained—, saturated or unsaturated—preferably saturated—, hydrocarbon chain of 2–5 and preferably 2–4 C atoms with two free binding sites.

Aryl in aryl and aralkyl residues is an aromatic ring system with 6 to 10 carbon atoms wherein phenyl is preferred.

Ammonium salts are those which contain the ammonium ion $NH_4^+$ or those which contain ammonium cations substituted once or several times by alkyl, aryl or aralkyl residues.

Alkali salts are preferably those of lithium, sodium or potassium. Alkaline earth salts are preferably those of magnesium or calcium.

Preferred residues $R^1$ are hydrogen and alkyl, in particular hydrogen.

Preferred residues $R^2$ are alkoxy residues and the amino group $NR^3R^4$.

A morpholine or thiomorpholine or piperazine residue formed by incorporation of the nitrogen atom of the general formula I is preferred within the meaning of an alkylene residue of $R^1$ and $R^3$ interrupted by oxygen, sulphur or nitrogen. A piperazine residue is particularly preferred.

An indoline or 1,2,3,4-tetrahydroquinoline residue formed by incorporation of the aromatic ring of the general formula I is preferred within the meaning of an alkylene residue formed from $R^1$ and $R^3$.

Salts of strong acids and in particular of mineral acids such as hydrochloric acid, sulphuric acid, nitric acid and phosphoric acid are preferred as the salt of a nitrosoaniline derivative of the general formula I according to the invention. Hydrochlorides are especially preferred i.e. salts of hydrochloric acid.

Preferred nitroso compounds of the general formula I are:
N,N'-Bis-(2-hydroxyethyl)-p-nitrosoaniline
N,N'-dimethyl-p-nitrosoaniline
N,N'-diethyl-p-nitrosoaniline
N-methyl-N'-(4-nitrosophenyl)-piperazine
N-(2-hydroxyethyl)-5-nitrosoindoline
2,4-dimethoxy-nitrosobenzene
N,N'-bis-(2-methoxyethyl)-4-nitrosoaniline
N-(4-nitrosophenyl)-morpholine
N-(2,2-diethoxy-ethyl)N'-(4-nitrosophenyl)-piperazine
p-nitrosophenol and
3-methoxy-4-nitrosophenol.

Among the electron-rich heteroaromatic nitroso compounds whose aromatic ring systems are so rich in electrons that an external +M substituent is not necessary for nitroso/oxime tautomerism or for imine formation, those that are particularly suitable for the method according to the invention are pyrazolones, pyrazoles and especially pyrazole compounds substituted by a nitroso group as described for example in Ullmann's Encyclopaedia of Industrial Chemistry 5th ed., Vol. A 20, pages 72 to 74. 3-Nitroso-pyrazolo compounds of the general formula II are particularly preferred in this case.

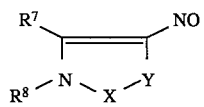

Most of these compounds are known from the U.S. Pat. No. 5,234,818 as precursors for the preparative synthesis of the corresponding 3-amino-pyrazolo compounds. In formula II X-Y denotes $NR^5$—CO or N=$CR^6$ $R^5$ denotes hydrogen, alkyl substituted if desired by hydroxy, carboxy, $SO_3H$, $PO_3H_2$, dialkylphosphinyl $R^6$ denotes hydrogen, alkyl, alkenyl, alkoxy, alkylthio, aryl, arylthio, aralkyl, each of which may be substituted if desired by hydroxy, carboxy, $SO_3H$, $PO_3H_2$, a salt of one of these acid residues or/and alkoxycarbonyl; or amino which is substituted if desired by one or two alkyl residues which if desired carry one or several hydroxy, carboxy, or/and alkoxycarbonyl residues, wherein if the amino is substituted by 2 alkyl residues, these residues can also be linked to form a ring which, apart from the N atom of the amino group, can also be interrupted if desired by oxygen, sulphur or a further nitrogen atom, or amino which is substituted if desired by one or two acyl groups, alkoxy or/and aralkoxycarbonyl groups, $H_2N$-CO, alkyl, aralkyl, or/and arylcarbamoyl groups; or carboxy, alkoxycarbonyl, carboxamido or halogen and $R^7$ denotes alkyl, thioalkyl or aralkyl, substituted if desired by hydroxy, carboxy, $SO_3H$ or $PO_3H_2$ or amino which is substituted if desired by one or two alkyl groups which in turn can be substituted by hydroxy, carboxy, $SO_3H$, dialkylphosphinyl or $PO_3H_2$, wherein at least $R^6$ and/or $R^7$ represent an amino group, and $R^8$ denotes an alkyl or aralkyl group which can be substituted if desired by hydroxy, carboxy, $SO_3H$ or $PO_3H_2$ or in which $R^7$ and $R^8$ together denote a saturated or unsaturated chain with 3 or 4 members composed of nitrogen atoms or of carbon atoms and if desired one or several nitrogen or sulphur atoms wherein carbon atoms are substituted if desired by alkyl, alkoxy, alkylthio, hydroxy, aralkyl, aryl, carboxy, carboxamido, alkoxycarbonyl, cyano, halogen, amino which is substituted if desired by one or two alkyl residues carrying if desired one or several hydroxy, carboxy or/and alkoxycarbonyl residues, and wherein nitrogen atoms that are not bound via a double bond are substituted by alkyl or aralkyl which if desired are substituted by hydroxy, $SO_3H$, $PO_3H_2$, carboxy or dialkylphosphinyl or two adjacent chain substituents if desired form an alkylene group which in turn is substituted if desired by aryl or is anellated as well as if desired the corresponding tautomeric forms and their salts.

In this case "alkyl"—also in alkylthio, dialkylphosphinyl, alkylcarbamoyl and aralkyl residues—denotes a straight-chained or branched alkyl residue with 1–6 and preferably 1–4 C atoms.

Examples are the methyl, ethyl, propyl, isobutyl or tert.butyl group.

If an amino group is substituted by 2 alkyl residues, these residues can also be linked to form a ring in such a way that as a whole they represent a ring interrupted by a nitrogen atom. In this case those amino groups are preferred which represent a ring with a total of 5 or 6 members and which itself is interrupted if desired by oxygen, sulphur or nitrogen. A morpholino residue is particularly preferred.

"Alkoxy"—also in alkoxy and aralkoxycarbonyl residues—represents a straight-chained or branched alkoxy residue with 1–6 and preferably 1–4 C atoms. Examples are the methoxy, ethoxy, propyloxy, isobutyloxy or tert.butyloxy group.

"Aryl"—also in arylcarbamoyl groups—denotes a carbon aromatic or heteroaromatic residue, preferably one with 6–10 ring atoms and in particular a phenyl and naphthyl group which can additionally be substituted by alkyl, alkoxy or/and halogen. A phenyl residue is particularly preferred.

An "aralkyl" residue—also in an aralkylcarbamoyl group—denotes a residue in which an alkyl group as defined above is substituted by an aryl residue as characterized above. A benzyl group is preferred.

An "aralkoxy" residue, as for example in aralkoxy-carbonyl groups, denotes a residue in which an alkoxy group as defined above is substituted by an aryl residue as characterized above. A benzyloxy group is preferred.

"Halogen" represents the residues fluorine, chlorine, bromine and iodine. Fluorine and chlorine are preferred.

An acyl group denotes a carboxylic acid residue which can contain alkyl, aralkyl or aryl residues. Acetyl, phenylacetyl or benzoyl residues are preferred.

An alkylene group is understood as a straight-chained or branched, saturated or unsaturated hydrocarbon chain with 3–5 and preferably 3 or 4 C atoms having two free binding sites.

Examples are —CH₂—CH=CH—

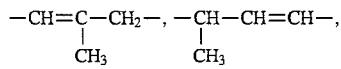

—(CH₂)₄— or —CH=CH—CH=CH—.

The butadiendiyl residue (—CH=CH—CH=CH—) and the tetramethylene residue (—(CH₂)₄—) are preferred.

An alkenyl residue is a straight-chained or branched hydrocarbon residue of 2–5 C atoms with at least one double bond. A vinyl residue is for example preferred. A dialkylphosphinyl group is understood as the residue

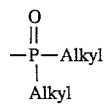

in which alkyl has the meaning stated above. A dimethylphosphinyl residue is preferred.

Alkali or alkaline earth salts or ammonium salts can be used as salts of SO₃H, PO₃H₂ and carboxy residues. Alkali salts are understood as lithium, sodium, potassium, rubidium and caesium salts wherein lithium, sodium and potassium salts and above all sodium and potassium salts are preferred. Alkaline earth salts are those of beryllium, magnesium, calcium, strontium or barium. Magnesium and calcium salts are preferred, calcium salts being particularly preferred. Salts of the unsubstituted ammonium ion NH₄⁺ can be used as ammonium salts. However, it is also possible to use those ammonium salts in which the ammonium ion is substituted by 1–4 alkyl, aryl or aralkyl residues. The definitions given above apply to these residues wherein methyl, ethyl and n-propyl are particularly preferred as the alkyl residue, a phenyl group is particularly preferred as the aryl residue and a benzyl group is particularly preferred as the aralkyl residue.

A carboxamido residue is understood as the residue CONH₂ and also those residues in which the amino group is substituted by one or two alkyl residues carrying if desired one or several hydroxy, carboxy or/and alkoxycarbonyl residues.

Those compounds are preferably used as nitroso compounds of the general formula II according to the invention in which R⁷ and R⁸ form a saturated or unsaturated chain as described above. In this connection it is particularly preferred if this chain is unsaturated and double bond electrons and free nitrogen electron pairs of the unsaturated chain are in conjugation with the double bond or with the bridging N atom of the general formula II so that an anellated aromatic ring is formed.

If desired tautomeric forms are also possible for a substance of the general formula II. It is intended to also encompass these in the general formula II.

Nitroso compounds of the general formulae III to XII are preferred according to the invention.

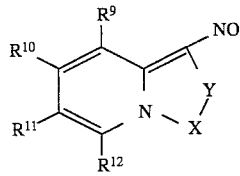

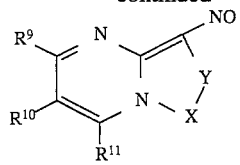

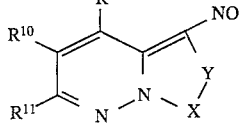

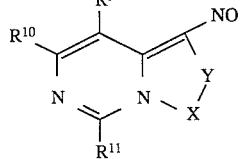

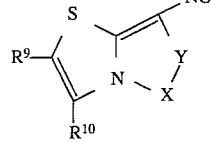

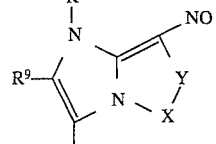

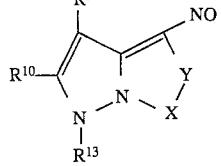

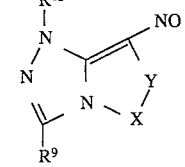

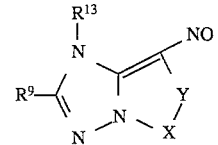

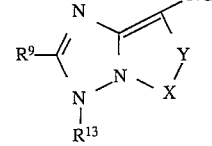

and if desired the corresponding tautomeric forms and their salts.

In this case X-Y has the same meaning as described above. R⁹, R¹⁰, R¹¹ and R¹² which are the same or different denote hydrogen, hydroxy, alkyl, alkoxy, alkylthio, aralkyl, aryl, carboxy, alkoxycarbonyl, carboxamido, cyano, amino which is substituted if desired by one or two alkyl residues carrying if desired one or several hydroxy, carboxy or/and alkoxycarbonyl residues or they denote halogen, wherein if desired two adjacent residues form an alkylene group which if desired is in turn substituted by aryl or is anellated and $R^{13}$ represents alkyl or aralkyl which can be substituted if desired by hydroxy, carboxy, $SO_3H$, $PO_3H_2$ or dialkylphosphinyl. The definitions of the residues correspond to those given for substances of the general formula II.

Although the range of suitable electron-rich aromatic nitroso compounds is very large, they are all accepted as direct electron acceptors by PQQ-dependent dehydrogenases. Only the nitroso group appears to be essential which is bound to an electron-rich aromatic residue.

The reaction can presumably be represented by the following reaction scheme using nitrosoaniline as an example:

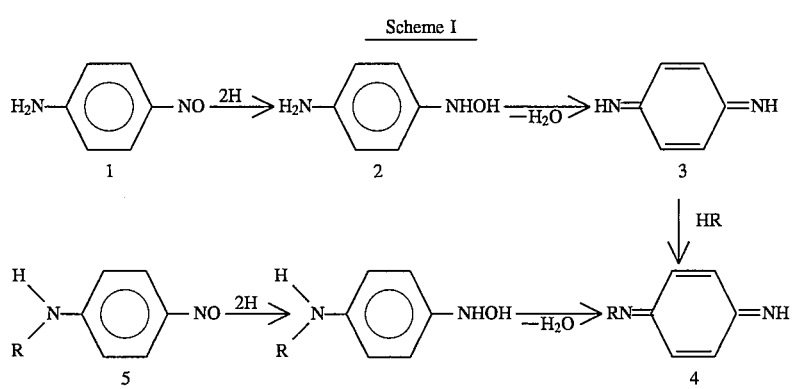

Scheme I

Substances of the general formulae III, IV, V, VII, VIII and IX and if desired the corresponding tautomeric forms and their salts are particularly preferred for the use according to the invention. Those substances are especially preferred in which X-Y has the meaning $N=CR^6$ in which $R^6$ can have the meaning as stated for the general formula II.

The compounds 3-nitroso-2-methyl-pyrazolo-[1.5a]-pyridine, 3-nitroso-pyrazolo-[1.5a]-pyridine and 3-nitroso-pyrazolo [3.2-c]-s-triazole and their salts, in particular the hydrochloride, have proven to be very well suited for the use according to the invention.

As set forth above, aromatic nitroso compounds are brought into contact with the sample to be examined and the PQQ-dependent dehydrogenase for the method according to the invention. In U.S. Pat. No. 5,206,147 and U.S. Pat. No. 5,122,244 it is described that oxidases and non-NAD-dependent dehydrogenases reduce aromatic nitroso compounds to electron-rich aromatic amino compounds which in turn can be detected by oxidative coupling using a chromogenic coupling reagent and an oxidizing agent.

Surprisingly it turned out that in the presence of a non-oxidative colour-forming detection reagent for quinoid imino compounds and a PQQ-dependent dehydrogenase, an aromatic nitroso compound is not completely reduced by PQQ-dependent dehydrogenase-catalysed enzymatic reduction to an electron-rich amine with concomitant oxidation of the analyte, but instead an imino intermediate formed after a partial enzymatic reduction can be captured and detected by the non-oxidative colour-forming detection reagent.

It was even more surprising that when certain aromatic nitroso compounds are selected which already carry a chromogenic residue, these aromatic nitroso compounds are reduced in the presence of a PQQ-dependent dehydrogenase to a coloured imino compound but there is essentially no further enzymatic reduction to the aromatic amine so that the coloured imino compound itself can also be determined as a measure of the amount of analyte without the necessity for reaction with a colour-forming detection reagent. Examples of appropriate chromogenic nitroso compounds which can be used according to the invention are given below.

The aromatic nitroso compound (1) is reduced, with concomitant oxidation of the analyte, to the aromatic hydroxylamine (2), this spontaneously cleaves off water to form a quinoid imino intermediate (3). Before this is further reduced enzymatically by the PQQ-dependent dehydrogenase to the aromatic amine, as known from U.S. Pat. No. 5,206,147 and U.S. Pat. No. 5,122,244, it can for example be captured by a coupling reagent (HR) and determined colorimetrically as a coloured coupling product (4) or it already contains the chromogenic residue of the coupling product in the starting compound (5) and can thus be directly determined colorimetrically as a coloured imino compound (4) after enzymatic reduction.

It is surprising that specifically when using PQQ-dependent dehydrogenases, the imino intermediate (3) can be specifically captured or directly detected according to the invention with a detection reagent without there being a further enzymatic reduction to form the amine as known from U.S. Pat. No. 5,204,147. Since when flavine-dependent oxidases are used which according to U.S. Pat. No. 5,204, 147 also reduce aromatic nitroso compounds, it is only possible to detect a small portion of the imino intermediate whereas the major portion of the imino intermediate is very rapidly enzymatically reduced further to the aromatic amine with concomitant oxidation of the analyte.

The detection of the imino compound can be achieved according to the invention by means of its intrinsic colour.

The detection of the quinoid imino compound can also be achieved according to the invention using a chromogenic non-oxidative reagent. Chromogenic means that a coloured substance is obtained by reaction of the colour-forming reagent with the imino compound whose absorption maximum is different from that of the nitroso compound used and the colour-forming reagent before the reaction. A non-oxidative chromogenic detection reagent is understood to mean that the detection reagent reacts with a compound to be detected and forms a colour without the detection reagent having an oxidative effect on the compound to be detected (e.g. by an additional oxidizing agent present in the detection reagent).

The detection of the imino compound formed in the method according to the invention can be achieved by reaction of a colour-forming coupling reagent with the imino compound. In this process a coloured substance is obtained which contains the imino compound as part of its structure. The detection can, however, also be achieved in that the imino compound oxidizes a leuco dye molecule to a coloured molecule.

It is also possible to combine both detection methods by coupling a coupling reagent with one molecule of the imino compound to be detected to form a non-coloured leuco dye molecule which is oxidized by a further molecule of the imino compound to form a dye.

Numerous colour-forming detection reagents of this kind for imino compounds are known. For example in principle all substances come into consideration which react with oxidized p-phenylenediamine derivatives to form a colour.

Examples of colour-forming coupling detection reagents are aromatic compounds, preferably phenol and naphthol compounds, which are substituted with good leaving groups and hence these leaving groups can be easily and very rapidly substituted by the imino compound to be detected with formation of colour. Preferred examples are 1-naphthol-4-sulfonic acid, 2,4,6-tribromo-3-hydroxybenzoic acid, 2,4-dichloro-1-naphthol, tatrazine or orange 1.

Detection reagents can also be used in the method according to the invention for the detection of the imino compound which do not couple to the imino compound but rather form a coloured compound during reduction of the imino compound to the amine. This often occurs with dimerization of the leuco dye. Suitable leuco dyes are known to a person skilled in the art from detection methods for $H_2O_2$ or peroxidase. Examples of such leuco dyes are inter alia 1-naphthylaminosulfonic acids, triarylimidazoles (U.S. Pat. No. 4,089,747) diaryl-imidazoles (U.S. Pat. No. 3,947,377), aminocarbazoles (U.S. Pat. No. 3,947,398), oxazoles, thiazoles U.S. Pat. No. 4,966,855).

All leuco dyes which as a result of their redox potential are able to reduce imino compounds are suitable.

Finally it is also possible to combine the detection method of coupling with a coupling reagent and oxidation of a leuco dye by using a reagent as the coupling component for imino compounds which forms a colourless leuco compound with the imino compound which is only oxidized to form a dye by a second molecule of the imino compound which is reduced to the corresponding aromatic amine. The most common so-called "couplers" which are very well known in colour photography are phenols, naphthols, anilines, naphthylamines as well as their derivatives and active methylene compounds. A review of this type of couplers is given by T. H. James in "The Theory of the Photographic Process" 3rd ed., Mc Millan, New York, 1966, chapter 17 on pages 385–390.

The method according to the invention is carried out in such a way that the sample to be examined is simultaneously contacted with a PQQ-dependent dehydrogenase, one or several of the electron-rich aromatic nitroso compounds described above and a detection reagent for imino compounds. If the sample contains an analyte which is oxidized by the PQQ-dependent dehydrogenase, the aromatic nitroso compound reacts to form the corresponding imino compound by enzymatic reduction. This reacts with the colour-forming detection reagent so that the colour which forms can be correlated with the concentration of the analyte in the sample. The measurement of the colour can be achieved directly by visual means using reference colours or photometrically.

A particularly simple method for the oxidative detection of analytes is then present when the imino compound which forms by reduction of the aromatic nitroso compound is itself coloured and does not have to be firstly detected by coupling with a colour-forming detection reagent or by oxidation of a leuco dye. As described above, coloured imino compounds are in fact known to a person skilled in the art from colour photography and from analytical methods of detection.

Nitrosoaniline compounds of formula XIII have proven to be particularly suitable as direct chromogenic electron acceptors for the method according to the invention for the oxidative detection of an analyte by direct measurement of a coloured quinoid imino compound, which are reduced to a coloured quinone diimine of formula XIV.

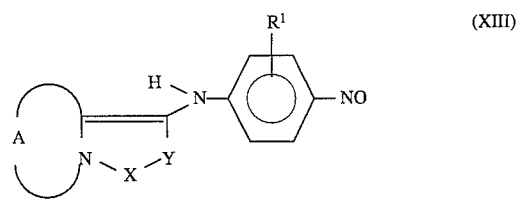

(XIII)

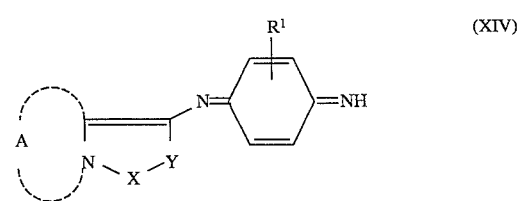

(XIV)

$R^1$ in the general formula XIII denotes hydrogen, hydroxy, halogen, alkoxy, alkylthio, aryloxy or arylthiol, alkyl substituted if desired by hydroxy, carboxy, $PO_3H_2$ or $SO_3H$, amino substituted if desired once or several times by alkyl which in turn can be substituted if desired by hydroxy, $PO_3H_2$, dialkyl-phosphinyl, $SO_3H$ or carboxy X-Y denotes $NR^5$—CO or $N=CR^6$ in which $R^5$ and $R^6$ have the same meaning as in the general formula II and A represents a saturated or unsaturated chain consisting of three members with a nitrogen or sulphur atom and two carbon atoms or two nitrogen atoms and one carbon atom, wherein the carbon atoms are substituted if desired by alkyl, alkoxy, alkylthio, hydroxy, aralkyl, aryl, carboxy, carboxamido, alkoxycarbonyl, cyano, halogen, amino which is substituted if desired by one or two alkyl residues carrying if desired one or several hydroxy, carboxy or/and alkoxycarbonyl residues, and wherein nitrogen atoms that are not bound via a double bond are substituted by hydrogen, alkyl substituted if desired by $SO_3H_2$ or dialkylphosphinyl, or by aralkyl or two adjacent chain substituents if desired form an alkylene group which in turn may be substituted if desired by aryl or is anellated, as well as if desired the corresponding tautomeric forms and their salts.

The meaning of the individual substitutents is in this case the same as in compounds of the general formula II.

In this case preferred residues for $R^1$ are hydrogen and alkyl and for X-Y the group $N=CR^6$, It is particularly preferred that A together with the adjacent heterocycle forms an imidazole, triazole, benzimidazole, thiazole or dihydroimidazole ring whose carbon atoms can carry the substituents stated in the general definition of A. In this case an imidazole ring is especially preferred.

Particularly preferred compounds are:
1) (2,4-dimethyl-pyrazolo-[1.5a]-imidazole-3-yl)-(4-nitrosophenyl)-amine
2) (4-methyl-pyrazolo-[1.5a]-imidazol-3-yl)-4-nitroso-phenyl)-amine 3) (4-(dimethylphosphinylmethyl)-2-methyl-pyrazolo-[1.5a]-imidazol-3-yl)-(4-nitrosophenylamine)
5) (5,6-dihydro-4-dimethylphosphinylmethyl-2-methyl-pyrazolo-[1.5a]-imidazol-3-yl)-(4-nitrosophenyl)-amine
6) (4-(dimethylphosphinylmethyl-2-methyl-pyrazolo-[1.5a]-imidazol-3-yl)-(4-nitrosophenyl)-amine and
7) 2,6-dimethyl-4-dimethylphosphinylmethyl-pyrazolo-[3.2c]-s-triazol-3-yl)-(4-nitrosophenyl)-amine If the method according to the invention is carried out in such a way that a coloured quinone diimine compound of formula XVII is formed directly by reduction of the aromatic nitroso compound, then the sample to be examined is contacted simultaneously with a PQQ-dependent dehydrogenase and one or several electron-rich aromatic nitroso compounds of the general formula XVI. If the sample contains an analyte which is oxidized by PQQ-dependent dehydrogenases, the electon-rich aromatic nitroso compound reacts to form the corresponding coloured quinone diimine. The additional abundance of electrons on the ring A condensed to the chromogenic electron-rich pyrazole ring has the surprising effect that the quinone diimine compound formed is no longer further enzymatically reduced to the corresponding amine but instead the coloured quinone diimine compound can be measured directly in the form of a measurement of light absorbance and can be correlated with the concentration of the analyte in the sample. In order to achieve a rapid enzymatic reduction of the chromogenic aromatic nitroso compounds, it is particularly advantageous when these are sufficiently soluble. When using chromogenic nitrosoaromatics of formula XIII, it is particularly advantageous for the method according to the invention when their concentration in solution is at least $10^{-3}$ mol/l and preferably at least $10^{-2}$ mol/l.

A good solubility can in particular be achieved by providing the chromogenic nitroso compound with hydrophilic groups.

Appropriate chromogenic nitroso compounds which are extremely well suited to the method according to the invention are for example the aforementioned compounds 3, 4 and 7.

The method can be carried out in a so-called wet test, for example in a cuvette or as a so-called dry test on an appropriate reagent carrier in which the necessary test reagents are present on a test carrier and in particular on an absorbent material or one capable of swelling. Such test carriers are for example known from U.S. Pat. No. 4,820,489, U.S. Pat. No. 4,876,067, U.S. Pat. No. 5,049,487.

The invention in addition concerns an agent for the colorimetric determination of an analyte by enzymatic oxidation as characterized in the claims. Such an agent contains in addition a colour-forming non-oxidative detection reagent for imino compounds apart from the PQQ-dependent dehydrogenase necessary for the enzymatic oxidation of the analyte to be determined and apart from at least one aromatic nitroso compound as a direct electron acceptor which accepts the electrons from the PQQ/dehydrogenase system released during the enzymatic oxidation of the analyte.

The substances described above for the method according to the invention are used as PQQ dehydrogenases, aromatic nitroso compounds and chromogenic detection reagents for quinoid imino compounds. If electron-rich aromatic nitroso compounds of formula XIII are used in the method according to the invention which already contain a chromogenic residue bound to the aniline nitrogen, then it is advantageous that the agent contains no colour-forming detection reagent for imino compounds since the quinone diimine of formula XIV formed during the reduction is already coloured.

In order to maintain a suitable pH value for the procedure which in particular depends on the enzymes used and the detection reagent for the imino compound, the agent according to the invention contains a buffer system. The agent preferably contains a buffer system which sets the pH in the test solution to a value between 4 and 9. A slightly acidic pH value between 5 and 6.5 is especially advantageous.

The agent according to the invention can be present in the form of a solution or drawn onto an absorbent carrier or one capable of swelling. When in the form of a solution, the agent preferably contains all reagents necessary for the method according to the invention. Water and also mixtures with water-soluble organic solvents such as for example methanol, ethanol, acetone or dimethylformamide preferably come into consideration as the solvent. For reasons of stability it may be advantageous to separate the reagents required for the test into two or several solutions which are not mixed until the actual examination. However, it is expedient to take care that the aromatic nitroso compound and the detection reagent for imino compounds are present in a solution before the test starts. The concentration of the aromatic nitroso compound used depends on the concentration of the analyte to be measured.

Typical concentrations for the analytes to be measured in the method according to the invention are $10^{-6}$–$10^{-2}$ mol/l and in particular $10^{-5}$–$10^{-3}$ mol/l. Accordingly, typical concentrations of the nitroso compounds used are $10^{-4}$–$10^{-1}$ mol/l. Concentrations of the nitroso compounds and in particular of the chromogenic nitroso compounds of formula XIV of more than $10^{-3}$ mol/l are particularly advantageous in order to achieve a sufficiently rapid enzymatic reduction. The concentration of the PQQ-dependent dehydrogenase used depends on its activity and the concentration of the analyte. Typical values for enzyme concentrations in cuvette tests are 1 mU/ml–1 U/ml.

Detection reagents for imino compounds are used in at least a stoichiometric ratio to the nitroso compounds used, preferably in a 1.5–2-fold excess.

The agent according to the invention can also be present in the form of a test strip. Such test strips are known in various embodiments, for example from U.S. Pat. No. 4,312,834 U.S. Pat. No. 4,820,489, U.S. Pat. No. 4,876,067, U.S. Pat. No. 5,049,487. In a test strip the reagents required in order to carry out the method of determination are present on solid carrier layers. Absorbent and/or swellable materials come into particular consideration as carrier layers which are wetted by the sample liquid to be examined. Examples are gelatin, cellulose or artificial fibre fleeces. The reagents are present in a solid form in or on these carrier materials. When the sample liquid is applied to the test strip or the test strip is immersed in the sample liquid, a liquid environment forms in the strip within which the detection reaction occurs. The colour formation caused by the reaction can be evaluated visually or photometrically, for example by reflection photometry.

The preferred concentrations of the individual reagents on the test strips are:

Analyte typically $10^{-4}$ to $10^{-1}$ M

Nitroso compound $10^{-3}$ to 1M

Non-oxidative detection reagent $10^{-3}$ to 1M

Enzyme 0.1 to 100 U per test zone.

The present invention offers the advantage that no unspecific reduction catalysts such as diaphorase or methylphenazinium-methosulfate are necessary for the reduction of an electron acceptor but instead its reduction is achieved directly by means of a specific analyte/enzyme system. Interfering side reactions can thus be avoided. By using nitroso compounds as electron acceptors, limitation of the electron acceptor by for example diffusion which is too slow as is the case when oxygen is used as an electron acceptor, no longer occurs. Only one equivalent of the analyte is oxidized per equivalent of the imino intermediate to be detected. This results in a high sensitivity of the analyte detection. Furthermore oxidizing agents are not required for the reaction with a colour-forming reagent. Therefore the entire detection reaction can also be carried out without interference in one step and in a common solution. The broad range of chromogenic detection reagents which can be used, including those which are known from colour photography, enable an almost free choice of the wavelength at which it is intended to carry out the measurement and of the absorption coefficient which determines the sensitivity of the measurement.

The method according to the invention is particularly easy to carry out when a coloured imino compound is formed directly and reaction with a chromogenic reagent becomes unnecessary.

The invention in addition concerns novel chromogenic nitrosoaniline compounds of formula XIII

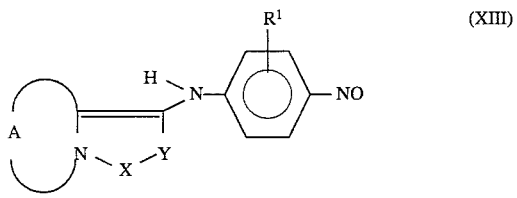

in which
$R^1$ denotes hydrogen, hydroxy, halogen, alkoxy or alkylthio, aryloxy or arylthio, alkyl substituted if desired by hydroxy, carboxy, $PO_3H_2$, alkyl, dialkyl-phosphinyl or $SO_3H$, amino substituted if desired once or several times by alkyl which in turn can be substituted if desired by hydroxy, $PO_3H_2$, $SO_3H$ or carboxy and denotes $NR^5$—CO or $N=CR^6$
X-Y denotes $NR^5$—CO or $N=CR^6$
in which $R^5$ denotes hydrogen, alkyl substituted if desired by hydroxy, carboxy, $SO_3H$, $PO_3H_2$, dialkylphosphinyl and
$R^6$ denotes hydrogen, alkyl substituted if desired by hydroxy, dialkylphosphinyl, carboxy, $SO_3H$, $PO_3H_2$, a salt of one of these acid residues or/and alkoxycarbonyl; or
amino which is substituted if desired by one or two alkyl residues carrying if desired one or several hydroxy, carboxy, or/and alkoxycarbonyl residues, wherein if the amino is substituted by 2 alkyl residues these residues can also be linked to form a ring which, apart from the N atom of the amino group, can also be interrupted if desired by oxygen, sulphur or a further nitrogen atom, or amino which can by substituted if desired by one or two acyl groups, alkoxy or/and aralkoxycarbonyl groups, $H_2N$—CO, alkyl, aralkyl, or/and arylcarbamoyl groups; or hydrogen, carboxy, alkoxycarbonyl, carboxamido or halogen and
A denotes a saturated or unsaturated chain consisting of three members with a nitrogen or sulphur atom and two carbon atoms or two nitrogen atoms and one carbon atom, wherein the carbon atoms are substituted if desired by alkyl, alkoxy, alkylthio, hydroxy, aralkyl, aryl, carboxy, carboxamido, alkoxycarbonyl, cyano, halogen, amino which is substituted if desired by one or two alkyl residues that if desired carry one or several hydroxy, carboxy or/and alkoxycarbonyl residues and wherein nitrogen atoms that are not bound via a double bond, are substituted by hydrogen, alkyl substituted if desired by hydroxy, $SO_3H$, carboxy, $PO_3H_2$ or dialkyl-phosphinyl, or by aralkyl or two adjacent chain substituents if desired form an alkylene group which in turn is substituted if desired by aryl or is anellated, as well as if desired the corresponding tautomeric forms and their salts.

The meaning of the individual substitutents is in this case the same as in the compound of the general formula II.

Preferred residues $R^1$ are hydrogen and unsubstituted or substituted alkyl. X-Y preferably forms the group $N=CR^6$ in which $R^6$ preferably represents hydrogen or unsubstituted or substituted alkyl.

It is particularly preferred that A together with the adjacent heterocycle forms an imidazole, triazole, benzimidazole, thiazole or dihydroimidazole ring in which the meaning of the ring substituents correspond with those of the general formula III.

It is particularly preferred that A forms an imidazole ring. Particularly preferred compounds are:
1) (2,4-dimethyl-pyrazolo-[1.5a]-imidazol-3-yl)-(4-nitrosophenyl)-amine
2) (4-methyl-pyrazolo-[1.5a]-imidazol-3-yl)-4-nitroso-phenyl)-amine
3) (4-(dimethylphosphinylmethyl)-2-methyl-pyrazolo-[1.5a]-imidazol-3-yl)-(4-nitrosophenylamine)
5) (5,6-dihydro-4-dimethylphosphinylmethyl-2-methyl-pyrazolo-[1.5a]-imidazol-3-yl)-(4-nitrosophenyl)-amine
6) (4-(dimethylphosphinylmethyl-2-methyl-pyrazolo-[1.5a]-imidazol-3-yl)-(4-nitrosophenyl)-amine
7) 2,6-dimethyl-4-dimethylphosphinylmethyl-pyrazolo-[3.2c]-s-triazol-3-yl)-(4-nitrosophenyl)-amine The compounds of formula XIII according to the invention are produced by well-known methods such as those described by J. T. Hays et al., in J. Org. Chem. 32, 158 (1967). For this ethers and preferably methyl ethers of p-nitrosophenol derivatives are reacted with appropriate 3-amino-heterocycles under proton catalysis. Secondary amines of formula XIII are formed by substitution of the methoxy group.

The hetarylamines used are either described in the literature or can be produced analogously to known methods. In particular amino compounds which contain pyrazolo heterocycles as the fundamental building blocks are described in U.S. Pat. No. 5,234,818.

The amino compounds required as intermediary products are usually present as salts of strong acids, e.g. mineral acids, for reasons of stability. The free bases of the amino compounds are preferably used for the reaction with p-nitrosoanisoles which are obtained by conventional methods e.g. by dissolving the salts in water, adding a base up to a pH of 8–10 and extracting the free base with an organic solvent such as ethyl acetate or methylene chloride. As an alternative one can use the following procedure in particular when the amino compounds are difficult to extract: the amino compound is dissolved in methanol, a base such as $NaHCO_3$ solution, triethylamine etc. is then added until the pH value of the methanol solution has reached a value of about 5–6 on a wet pH paper. Subsequently the second reaction partner, p-nitrosoanisole is added.

EXAMPLE 1

Determination of glucose using PQQ-dependent glucose-dye oxidoreductase and 1-naphthol-sulfonic acid as a coupling reagent.

The following were mixed in a cuvette:

| | |
|---|---|
| Citrate buffer/pyrophosphate buffer (50 mM) pH 7.5 | 0.38 ml |
| N,N-Bis(2-hydroxyethyl)-4-nitrosoaniline (5 mM in buffer) | 0.40 ml |
| 1-Naphthol-4-sulfonic acid (10 mM in H$_2$O) as the coupling reagent | 0.20 ml |
| Sample solution (0–40 mM glucose) | 0.01 ml |

Figure 1:
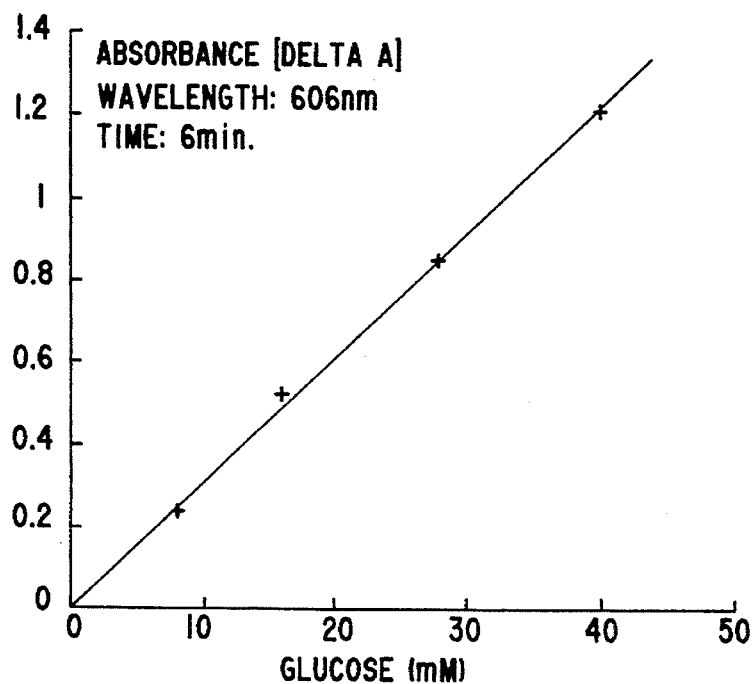
FIG. 1 shows the results of a determination of glucose using PQQ-dependent glucose-dye oxidoreductase and 1-naphthol-sulfonic acid as a coupling reagent.

The test was started by addition of 0.01 ml enzyme solution (glucose dye oxidoreductase, EC 1.1.99.17, 900 U/ml, 800 U/ml) and the change in absorbance was measured at 606 nm. Constant absorbance values were achieved after a maximum of 5 minutes (FIG. 1).

EXAMPLE 2

Detection of glucose using PQQ-dependent glucose dye oxidoreductase and 2,4,6-tribromo-3-hydroxybenzoic acid as the detection reagent.

| Measurement mixture (final concentrations) | |
|---|---|
| 100 mM | citrate buffer pH 5.8 |
| 10 mM | 2,4,6-tribromo-3-hydroxybenzoic acid |
| 1 mM | N,N-bis-(2-hydroxyethyl)-4-nitrosoaniline |
| 10 U/ml | glucose dye oxidoreductase |
| 0.1 M | sodium nitrate |
| 100–500 mM | glucose |

Figure 2:
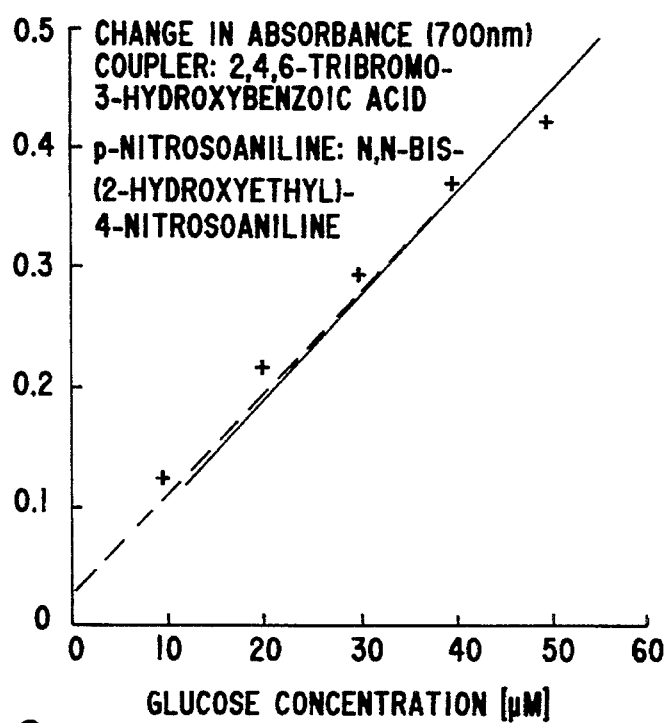
FIG. 2 shows the results of glucose detection using PQQ-dependent glucose dye oxidoreductase and 2,4,6-tribromo-3-hydroxybenzoic acid as the detection reagent.

An increasing formation of a green dye is observed with increasing glucose concentration (max.= 700 nm, FIG. 2).

EXAMPLE 3

The other coupling reagents for imines shown in Table 1 can be used in the same way. Table 1 shows the absorption maxima obtained after coupling N,N-bis-(2-hydroxyethyl)-p-quinonediimine with the listed couplers.

TABLE 1

| Coupler | Colour | λmax:nm | Remarks |
|---|---|---|---|
| N-phenyl-N-methyl-amino-methylphosphonic acid | blue-green | 740 | |
| N-methylanthranilic acid | green | 720 | narrow band |
| jujolodine | turquoise | 710 | broad band |
| 2,4,6-tribromo-3-hydroxybenzoic acid | green | 705 | |
| 1-naphthol-2-sulfonic acid | blue | 640 | |
| 3,4,5-trimethoxybenzoic acid | blue-green | 610 | |
| 3-methyl-1-phenyl-2-pyrazolin-5-one | violet | 565 | |
| acetic acid anilide | orange | 455 | broad band |
| 2,4-dichloro-1-naphthol | blue | 600 (670 sh) | bleaches slowly |
| 4-bromo-2,6-dimethyl-phenol | blue | 600 | stable |
| 3-phenyl-5-isoxazolone | lilac | 565 | |
| benzoylacetonitrile | red (violet) | 515 | intensive, brilliant |
| cyanacetanilide | orange-red | 490 | |
| [structure: N-methylindole fused with N-methyl oxindole =O] | blue | 595 | brilliant colour |
| [structure: pyrazolo-pyridine –OH] | blue-grey | 590 | fades to yellow |

TABLE 1-continued

| Coupler | Colour | λmax:nm | Remarks |
|---|---|---|---|
| 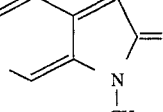 | blue-grey | 605 | fades to grey-reddish |
| 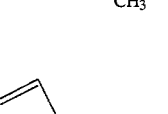 | violet | 550 | weak colouration |
| tartrazine | green | 610 | mixed colour |
| orange 1 | blue | ca. 650 | |
| 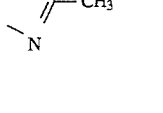 | blue | ca. 600 | |

EXAMPLE 4

Various electron-rich aromatic nitroso compounds listed in Table 2 were used analogously to example 1. Table 2 gives the colours and absorption maxima obtained after coupling with 1-naphthol-2-sulfonic acid or 1-naphthol- 4-sulfonic acid.

TABLE 2

| Nitroso compound | Coupler | Colour | λmax:nm |
|---|---|---|---|
| | 1-naphthol-4-sulfonic acid | violet | 530 |
| | 1-naphthol-4-sulfonic acid | purple | 530 |
| | 1-naphthol-4-sulfonic acid | violet to blue | 610 |
| | 1-naphthol-4-sulfonic acid | " | 610 |

TABLE 2-continued

| Nitroso compound | Coupler | Colour | $\lambda_{max}$:nm |
|---|---|---|---|
| O=N—C6H4—N(indoline)—C2H4—OH | 1-naphthol-4-sulfonic acid | " | 640 |
| O=N—C6H4—N(piperazine)—N—CH3 | 1-naphthol-4-sulfonic acid | " | 550 |
| O=N—C6H4—N(morpholine) | 1-naphthol-4-sulfonic acid | " | 550 |
| O=N—C6H4—N(CH2—CH2—O—CH3)2 | 1-naphthol-4-sulfonic acid | " | 595 |
| O=N—C6H4—N(indoline)—CH3 | 1-naphthol-4-sulfonic acid | " | 605 |
| O=N—C6H3(OCH3)—O—CH3 | 1-naphthol-4-sulfonic acid | " | 520 |
| O=N—C6H4—N(piperazine)—N—CH2—CH(OC2H5)2 | 1-naphthol-4-sulfonic acid | " | 550 |
| O=N—C6H4—N(piperazine)—N—CH2—CH2—C(=O)—O—C2H5 | 1-naphthol-4-sulfonic acid | " | 540 |

EXAMPLE 5

Comparison of glucose determination by means of the detection of imino compounds by reductive couplings between PQQ-dependent glucose dye oxidoreductase and glucose oxidase.

The following are placed in a cuvette:

| | |
|---|---|
| 100 mM | phosphate buffer pH 7.5 |
| 1 mM | N,N-bis-(2-hydroxyethyl)-4 nitrosoaniline |
| 10 mM | 1-naphthol-4-sulfonic acid |
| 100 U/ml | glucose dye oxidoreductase |

Figure 3:
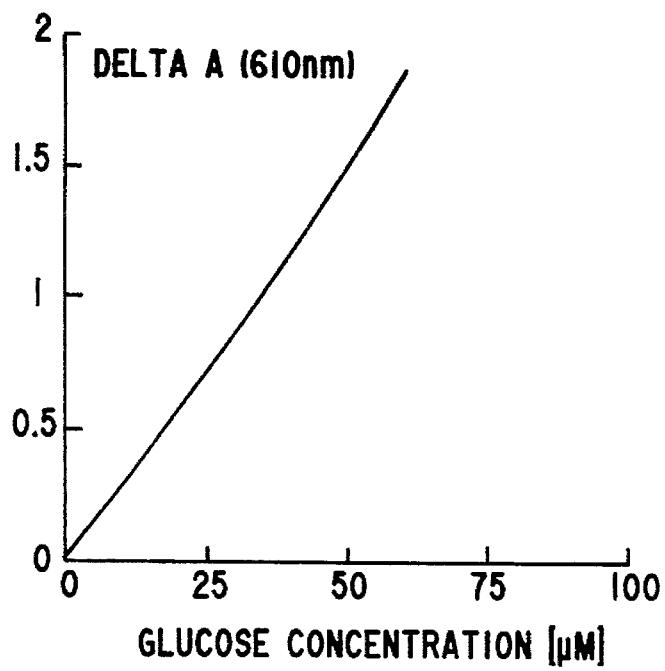
FIG. 3 shows the results of glucose determination by means of the detection of imino compounds by coupling reactions using PQQ-dependent glucose dye oxidoreductase.

The corresponding amounts of colour are obtained by addition of glucose (0–60 mM) (FIG. 3).

Figure 4:
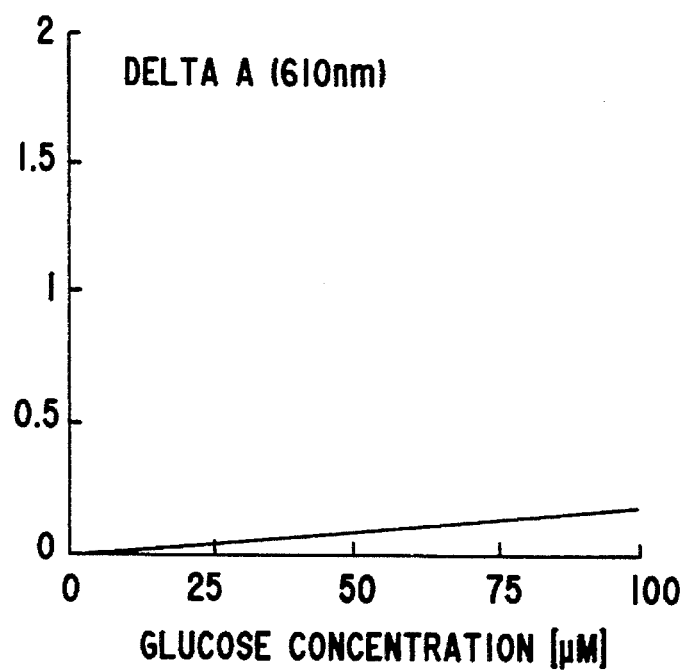
FIG. 4 shows the results of glucose determination by means of the detection of imino compounds by coupling reactions using glucose oxidase.

If the glucose dye oxidoreductase is replaced by the same amount of glucose oxidase, the amount of colour generated is 8 times lower since a major portion of the quinone diimine intermediate which forms is reduced further by glucose oxidase to form phenylenediamine with consumption of glucose (FIG. 4).

EXAMPLE 6

Determination of glucose using PQQ-dependent glucose dye oxidoreductase by means of reductive formation of coloured imino compounds.

Reaction equation

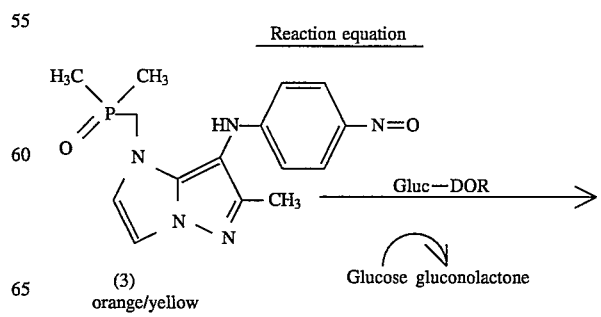

(3) orange/yellow

Gluc—DOR

Glucose gluconolactone

-continued
Reaction equation

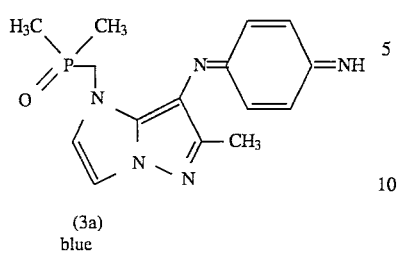

(3a) blue

Figure 5:
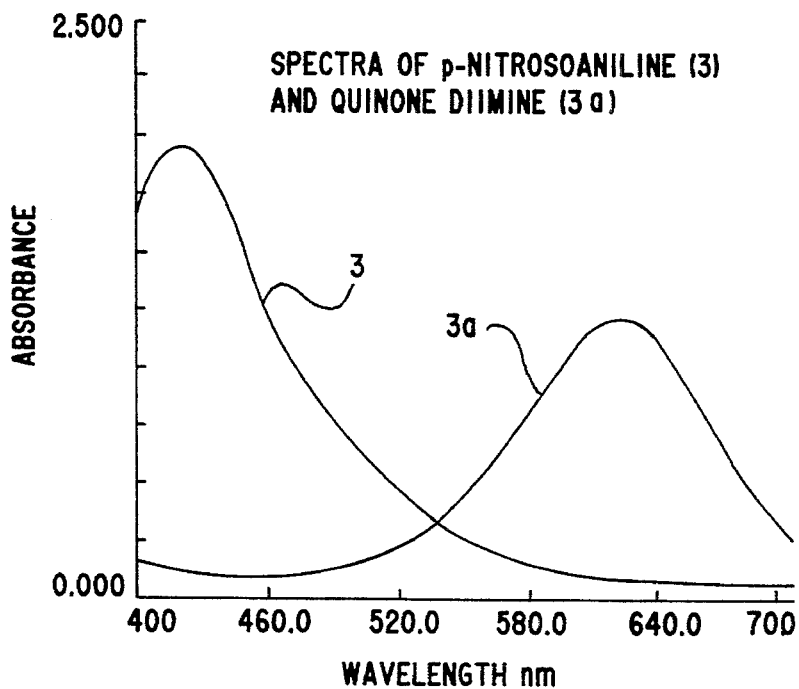
FIG. 5 shows the spectra of p-nitrosoaniline and quinone diimine.

The spectra of (3) and (3a) are shown in FIG. 5.

| 200 mM | citrate buffer pH 6 |
| 1 mM | p-nitrosoaniline (No.3 from TABLE 3) |
| 1 mM | $CaCl_2$ 20 U/ml mutarotase |
| 10 U/ml | glucose dye oxidoreductase |

Figure 6:
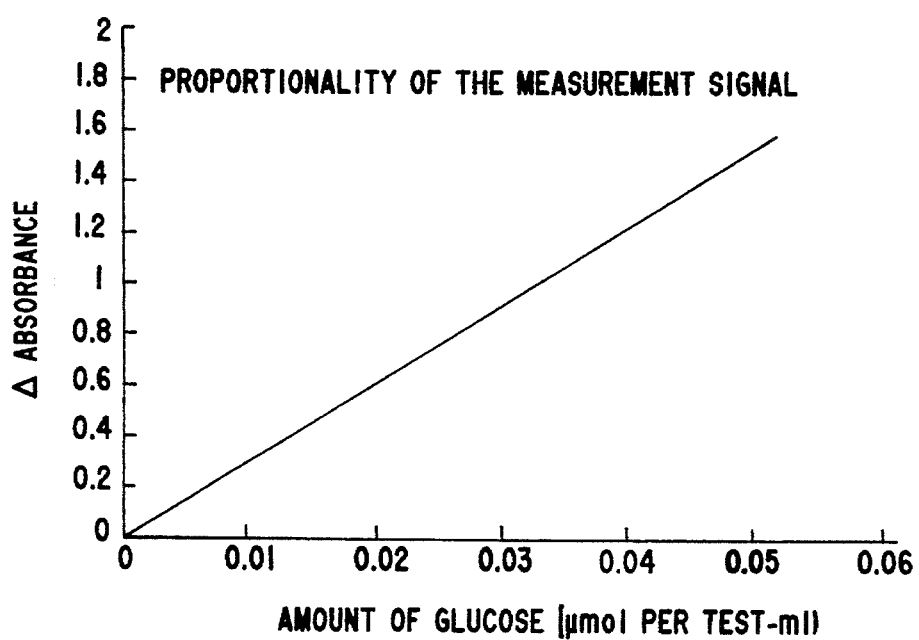
FIG. 6 shows the results of glucose determination by means of reductive formation of colored imino compounds using PQQ-dependent glucose dye oxidoreductase.

The changes in absorbance were measured 5 minutes after addition of various amounts of glucose between 0 and 50 μM final concentration (FIG. 6).

The compounds of Table 3 are used analogously. Table 3 shows the absorption maxima of the nitroso compounds used and of the coloured quinone diimes which are formed.

TABLE 3

| No. | structure | solubility in water | $\lambda_{max}$(nm) of the p-nitrosoaniline | $\lambda_{max}$(nm) of the quinone diimine |
|---|---|---|---|---|
| 1 | (structure) | −1 mM | 420 | 615 |
| 2 | (structure) | −1 mM | 430 | 590 |
| 3 | (structure) | −10 mM | 430 | 620 |
| 4 | (structure) | −10 mM | 430 | 620 |
| 5 | (structure) | −0.1 mM | 420 | 630 |

TABLE 3-continued

| No. | structure | solubility in water | $\lambda_{max}$(nm) of the p-nitrosoaniline | $\lambda_{max}$(nm) of the quinone diimine |
|---|---|---|---|---|
| 6 | (structure) | 10 mM | 420 | 610 |
| 7 | (structure) | 10 mM | 420 | 617 |
| 8 | (structure) | 0.2 mM | 430 | 590 |

EXAMPLE 7

Determination of the enzyme activity of a PQQ-dependent glucose dye oxidoreductase by means of reductive formation of a coloured imino compound from an aromatic nitroso compound.

The reaction described in example 6 can also be used to measure the enzyme activity of a PQQ-dependent dehydrogenase.

| Measurement mixture (final concentration) | |
|---|---|
| 200 mM | citrate buffer pH 5.8 |
| 1 mM | p-nitrosoaniline (3) from example 6 |
| 1 mM | CaCl$_2$ |
| 30 mM | glucose |

Figure 7:
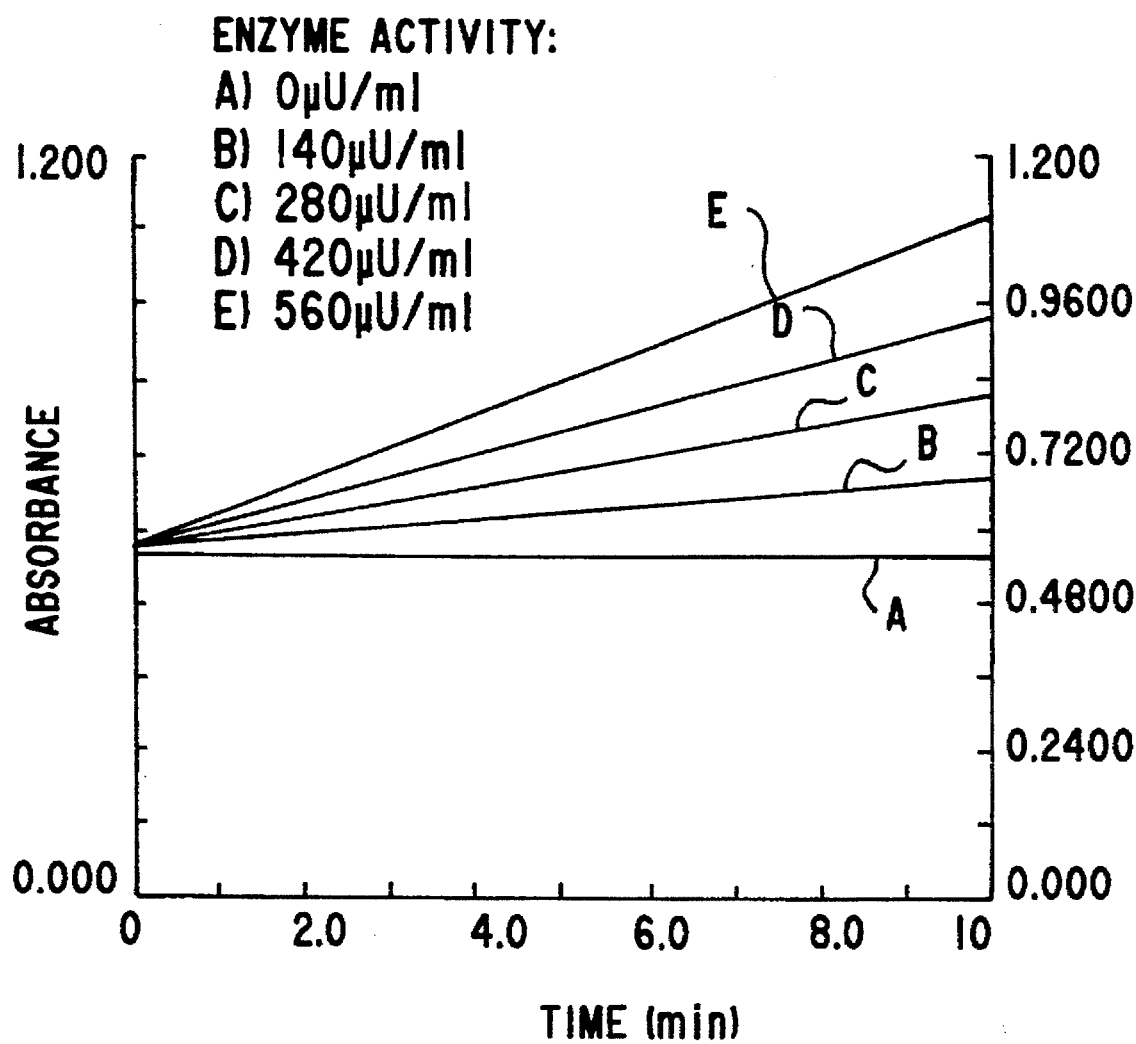
FIG. 7 shows the results of a determination of the enzyme activity of a PQQ-dependent glucose dye oxidoreductase by means of reductive formation of a colored imino compound from an aromatic nitroso compound.

The kinetic measurement was started with 0–1 mU glucose dye oxidoreductase and the change in colour was measured with regard to time (FIG. 7).

EXAMPLE 8

(4-(dimethylphosphinylmethyl)-2-methyl-pyrazolo-[1.5a]-imidazol-3-yl)-(4-nitrosophenyl)-amine (3)

13.7 g 3-amino-2-methyl-4-(dimethylphosphinylmethyl)-pyrazolo-[1.5a]-imidazole dihydrochloride is dissolved in 350 ml methanol. The solution is cooled to ca. 5° C. and concentrated aqueous sodium bicarbonate solution is added until a pH value of ca. 6 is indicated on a wet pH paper. A solution of 7.8 g p-nitrosoanisole in 35 ml methanol is added dropwise within 30 minutes. The mixture is stirred at room temperature for 4 hours and the pH value is kept at 6 by addition of more NaHCO$_3$ solution.

The reaction mixture is filtered, mixed with ca. 150 ml silica gel and evaporated to dryness. The silica gel is packed onto a silica gel column and the product is isolated by eluting with toluene/methanol 2:1. 10.3 g of a black-brown mass is obtained which is again chromatographed on silica gel with methylene chloride/methanol 12:1. 4.9 g of the title compound is obtained with an Fp. of 204° C. (while decomposing).

R$_f$(silica gel) toluene/methanol 2:1 = 0.3
CH$_2$Cl$_2$/methanol 12:1 = 0.21

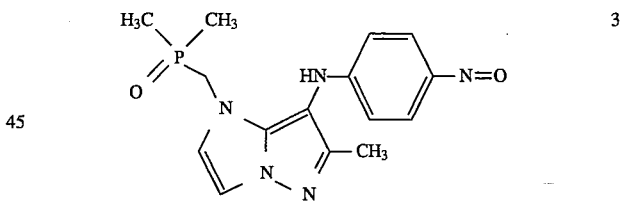

3

Production of the Starting Product a) 4-Dimethylphosphinylmethyl-2-methyl-pyrazolo-[1.5a]-imidazole 37 g 2-methyl-pyrazolo-[1.5a]-imidazole (J. Het. Chem. 10, 441 (1973)) is dissolved in 370 ml dry dimethylformamide and admixed with 54.2 g chloromethyldimethylphosphanoxide and 119 g potassium carbonate. The mixture is stirred for 10 hours at 115° C. (bath temperature). The precipitate is filtered by suction and the filtrate is concentrated by evaporation. The residue is chromatographed on silica gel (mobile solvent: ethyl acetate/methanol 2:1). A total of 36.6 g the title compound is obtained as a mixture of brown crystals and a brown oil. TLC (silica gel, ethyl acetate/methanol 2:1) R$_f$=0.2 b) 3-Amino-4-dimethylphosphinylmethyl-2-methyl-pyrazolo-[1.5a]-imidazole×2 HCl 18 g of the compound obtained above is dissolved in 25 ml concentrated hydrochloric acid and 50 ml water. A solution of 6.2 g sodium nitrite in 25 ml water is added dropwise at 0° C. After 30 minutes at 0° C. the solution is made weakly alkaline by addition of sodium bicarbonate solution and then 21.4 g sodium dithionite is added in portions. The mixture is stirred for a further 30 minutes and admixed with a solution of 17 g di-tert.-butyldicarbonate in 100 ml dioxane. The reaction mixture is stirred overnight at room temperature, the dioxane is removed by distillation and the residue is extracted several times with n-butanol/ethyl acetate 3:1. The residue that remains after drying and evaporating the organic phase is dissolved in 320 ml methanol saturated with HCl. It is stirred for a further 2 hours, cooled in an ice bath and the precipitated crystals are filtered. A total of 18.1 g of the title compound is obtained. TLC (silica gel, toluene/methanol 3:1) $R_f$=0.1

EXAMPLE 9

(4-Nitrosophenyl)-2-methyl-4-sulfopropyl-pyrazolo-[1.5a]-imidazol-3-yl)-amine (4)

3-Amino-4-sulfopropyl-pyrazolo-[1.5a]-imidazole is reacted with p-nitrosoanisole in methanol analogously to example 7. The reaction mixture is filtered and the filtrate is concentrated by evaporation. The residue is chromatographed on silica gel using toluene/methanol 2:1. The product is then applied to a column with the adsorber resin HP 208S (Mitsubishi Co.) for further purification and eluted with a stepwise gradient of methanol/water 1:9 to 2:8. The fractions containing the product are pooled, concentrated, taken up in a small amount of ethanol and the product is precipitated by addition of ether. The title product is obtained in the form of a brown powder.

TLC (silica gel, ethanol: $R_f$=0.6, isopropanol/butyl acetate/water 5:3:2 $R_f$=0.48)

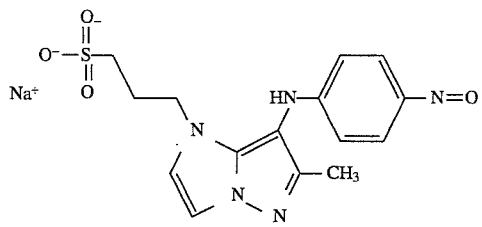

Production of the Starting Product a) 2-Methyl-4-sulfopropyl-pyrazolo-[1.5a]-imidazole 2-Methyl-pyrazolo-[1.5a]-imidazole is reacted at pH 2–5 with phenyldiazonium salt which is obtained from aniline in the usual way by diazotizing. The 2-methyl-3-phenylazo-pyrazolo-[1.5a]-imidazole (5.6 g) obtained is dissolved in 60 ml dimethyl-formamide and admixed with 3.4 g propane-sulfone and 7 g potassium carbonate. The mixture is stirred for 6 hours at 110° C., 5 g propanesulfone and 7 g potassium carbonate are again added and it is stirred for a further 8 hours at 110° C. After cooling it is filtered and the residue is washed well twice with methanol. The solution is concentrated and the residue is separated by means of chromatography on silica gel (mobile solvent: ethyl acetate/methanol/water 75:15:10).

Yield: 5.3 g yellow-brown crystals TLC (silica gel, ethyl acetate/methanol/water 75:15:10) $R_f$=0.3 b) 3-Amino-2-methyl-4-sulfopropyl-pyrazolo-[ 1.5a ] -imidazole 4.3 g of the azo compound obtained above is dissolved in 40 ml glacial acetic acid and 4 g zinc powder is added in portions within 1 hour. The mixture is stirred for a further 30 minutes, filtered by suction and evaporated. The residue is triturated with 30 ml ethyl acetate, filtered by suction and the filtrate is discarded. 10.2 g of a grey-brown powder is obtained which is sufficiently pure for further processing.

TLC (silica gel, ethyl acetate/acetone/glacial acetic acid/water 5:2:2:1) $R_f$=0.14

EXAMPLE 10

The compounds of Table 4 were produced analogously to examples 8 or 9. The synthesis of the amino starting compounds is carried out in the following manner:

a) Production of the starting compound for 5 in Table 4: 3-Amino-5,6-dihydro-, 4-dimethylphosphinylmethyl-2-methyl-pyrazolo-[ 1.5a ] -imidazole 3.9 g 2-methyl-pyrazolo-[1.5a]-imidazoline, 2.7 g sodium acetate and 7.4 g p-methoxybenzenediazonium tetrafluoroborate are dissolved in 40 ml glacial acetic acid and the solution is heated for 1 hour to 40°–50° C. The reaction mixture is evaporated, the residue is taken up in NaHCO₃ solution and ethyl acetate. It is extracted with ethyl acetate, dried and concentrated by evaporation. The residue is purified by chromatography on silica gel (mobile solvent: ethyl acetate/ligroin 1:1–2:1; ethyl acetate; ethyl acetate/methanol 95:5). 4.12 g of the corresponding 3-azo compound is obtained (TLC: silica gel, ethyl acetate/methanol 95:5; $R_f$=0.5) which is alkylated with chloromethyldimethylphosphanoxide on the nitrogen of the imidazoline ring. Conversion into the 3-amino compound is carried out analogously to example 8b by reduction of the azo group.

For the isolation and purification, the crude amino compound is dissolved in a small amount of water, admixed with solid sodium bicarbonate and a solution of the three-fold molar amount of di-tert.-butyldicarbonate in dioxane is added. The mixture is stirred overnight, evaporated, firstly extracted with ether in order to removed by-products and then extracted 5 times with methylene chloride in order to isolate the product. The crystalline t-butoxycarbonyl compound is obtained (TLC: ethyl acetate/acetone/glacial acetic acid/water 50:25:12:5:12,5, $R_f$=0.5) which is dissolved in 50 ml methanolic hydrochloric acid in order to cleave the tert.butoxycarbonyl group. After 1 hour at room temperature, it is concentrated to half the volume and the product is precipitated with ether. The title compound is obtained as a hydrochloride. TLC: n-butanol/glacial acetic acid/water 2:1:1 $R_f$=0.3 b) Production of the starting compound for 6 in Table 4: 3-Amino-4-dimethylphosphinylmethyl-2-methyl-pyrazolo-[ 1.5a] -benzimidazole The title compound is obtained analogously to example 10 by reacting 2-methyl-pyrazolo-[1.5a]-benzimidazole (J. prakt. Chem. 325, 829 (1984)) with phenyldiazonium salt, N-alkylation with chloromethyl-dimethylphosphanoxide and reduction of the azo group with zinc in glacial acetic acid. The title compound is obtained as a trihydrochloride-dihydrate of Fp. 192 (decomposition) TLC: silica gel, isopropanol/butyl acetate/water 50:30:20) $R_f$=0.38 c) Production of the starting compound for 7 in Table 4: 3-Amino-2,6-dimethyl-4-dimethylphosphinyl-pyrazolo-[ 3.2c] -s-triazole 6 g 2,6-dimethyl-pyrazolo-[3.2c]-s-triazole is dissolved in 65 ml dimethylformamide and the solution is admixed with 3.9 g chloromethyl-dimethylphosphanoxide and 8 g potassium carbonate. The mixture is stirred for 2 hours at 100° C., it is filtered by suction while hot and the filtrate is concentrated by evaporation. The residue is chromatographed on silica gel (mobile solvent: ethyl acetate/methanol 4:1). The product is heated for 7 hours in concentrated hydrochloric acid under reflux for saponification and decarboxylation. The reaction mixture is evaporated. A light-brown oil is obtained. TLC (silica gel: ethyl acetate/methanol 2:1) $R_f$=0.37

The conversion of the product obtained above into the 3-amino compound is carried out analogously to the method (8b) described in example 8 for the corresponding 3-aminopyrazolo-[1.5a]-imidazole. The title compound is obtained as a hydrochloride of Fp. 225° C. (decomposition). TLC (silica gel ethyl acetate/methanol 3:1) $R_f$=0.2

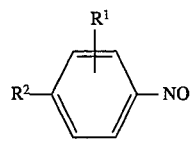

wherein $R^1$ is selected from the group consisting of hydrogen; hydroxy; an alkyl which is unsubstituted or substituted by hydroxy, COOH, $PO_3H_2$, or $SO_3H$; alkoxy; alkylthio; aryloxy; arylthio; halogen; and an amino which is unsubstituted or substituted at least once by an alkyl which is unsubstituted or substituted by hydroxy, $PO_3H_2$, dialkylphosphinyl, $SO_3H$ or $CO_2H$;

TABLE 4

| Structure | Fp. (°C.) | Comments |
|---|---|---|
| 5 (structure) | 212–215 (decomp.) | TLC (silica gel) $R_f$= 0.5 ethyl acetate/acetone/glacial acetic acid/water 50:25:12.5.12.5 |
| 6 (structure) | 222–224 | TLC (silica gel) $R_f$= 0.19 methylene chloride/methanol 20:1 |
| 7 (structure) | above 132 (decomp) | TLC (silica gel) $R_f$= 0.24 ethyl acetate/methanol 4:1 |

We claim:

1. A method for the colorimetric determination of an analyte, comprising, enzymatically oxidizing an analyte with an oxidoreductase in the presence of a direct electron acceptor, wherein said direct electron acceptor is an electron-rich aromatic nitroso compound, wherein the electron-rich aromatic nitroso compound is reduced enzymatically in the presence of a pyrroloquinoline quinone (PQQ)-dependent dehydrogenase to an imino compound with concomitant oxidation of the analyte without further enzymatic reduction to an aromatic amine, reacting said imino compound with a non-oxidative chromogenic detection reagent, and measuring any color formation.

2. The method according to claim 1, wherein said aromatic nitroso compound is a compound of formula I:

$R^2$ is selected from the group consisting of a hydroxy group, an alkoxy group, an aryloxy group, an arylthio group, an alkylthio group, an amino group which is unsubstituted or substituted at least once by alkyl, $PO_3H_2$, $SO_3H$, $CO_2H$, or an ammonium, alkali or alkaline earth salt form of $PO_3H_2$, $SO_3H$, or $CO_2H$, and an amino group $NR^3R^4$ wherein said alkoxy, aryloxy arylthio or alkylthio groups are unsubstituted or the alkyl residue is substituted by a hydroxy group, and $R^3$ and $R^4$ are individually selected from the group consisting of hydrogen, an aryl group, an alkyl group, an alkoxy group, a hydroxyalkoxy group, a polyalkoxy group which is unsubstituted or substituted by hydroxy, $PO_3H_2$, $SO_3H$, COOH, or a salt form of $PO_3H_2$, $SO_3H$ or COOH, and an amino group which is unsubstituted or substituted at least once by an alkyl group, wherein said aryl group and said alkyl group are unsubstituted or substituted by a hydroxy.

3. The method according to claim 2, wherein said aromatic nitroso compound is a compound selected from the group consisting of the compounds of formula III–XII:

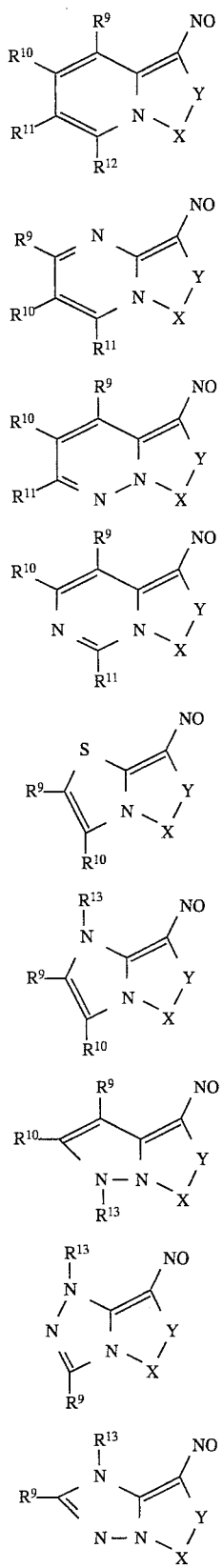

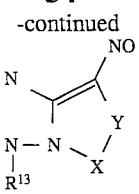

wherein X-Y is selected from the group consisting of $NR^5$—CO and $N=CR^6$, $R^5$ is selected from the group consisting of hydrogen, an alkyl group which is unsubstituted or substituted by a residue selected from the group consisting of hydroxy, carboxy, $SO_3H$, $PO_3H_2$, and dialkylphosphinyl, $R^6$ is selected from the group consisting of hydrogen, alkyl, alkenyl, alkoxy, alkylthio, aryl, arylthio, aralkyl, dialkylphosphinyl, and an amino which is unsubstituted or substituted by one or two alkyl residues which in turn are unsubstituted or substituted by at least one hydroxy, carboxy, or alkoxycarbonyl residues, wherein said alkyl, alkenyl, alkoxy, alkythio, aryl, arylthio, and aralkyl groups are unsubstituted or substituted by hydroxy, carboxy, $SO_3H$, $PO_3H_2$, a salt of $SO_3H$, a salt of $PO_3H_2$, or alkoxycarbonyl, $R^9$, $R^{10}$, $R^{11}$ and $R^{12}$ are individually selected from the group consisting of hydrogen, hydroxy, alkyl, alkoxy, alkylthio, aralkyl, aryl, carboxy, alkoxycarbonyl, carboxamido, cyano, halogen, and an amino which is unsubstituted or substituted by one or two alkyl residues which are unsubstituted or substituted by at least one hydroxy, carboxy or alkoxycarbonyl residues; wherein two adjacent residues form an alkylene group which is unsubstituted or substituted by aryl or is anellated, and $R^{13}$ is selected from the group consisting of alkyl and aralkyl wherein said alkyl and aralkyl are unsubstituted or substituted by hydroxy, carboxy, $SO_3H$, $PO_3H_2$ or dialkylphosphinyl.

4. The method according to claim 1, wherein said aromatic nitroso compound is a compound of formula I:

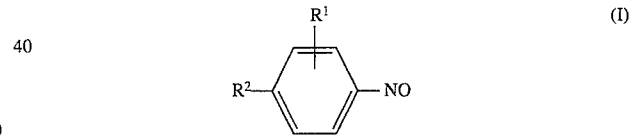

wherein $R^1$ is selected from the group consisting of hydrogen; hydroxy; an alkyl which is unsubstituted or substituted by hydroxy, COOH, $PO_3H_2$, or $SO_3H$; alkoxy; alkylthio; aryloxy; arylthio; halogen; and an amino which is unsubstituted or substituted at least once by an alkyl which is unsubstituted or substituted by hydroxy, $PO_3H_2$, dialkylphosphinyl, $SO_3H$ or $CO_2H$;

$R^2$ is selected from the group consisting of a hydroxy group, an alkoxy group, an aryloxy group, an arylthio group, an alkylthio group, an amino group which is unsubstituted or substituted at least once by alkyl, $PO_3H_2$, $SO_3H$, $CO_2H$, or an ammonium, alkali or alkaline earth salt form of $PO_3H_2$, $SO_3H$ or $CO_2H$, and an amino group $NR^3R^4$ wherein said alkoxy aryloxy arylthio or alkylthio groups are unsubstituted or the alkyl residue is substituted by a hydroxy group, and $R^3$ and $R^4$ form an alkylene residue which is uninterrupted or interrupted by oxygen, sulphur or nitrogen, wherein said nitrogen is substituted by a residue selected from the group consisting of an alkyl, hydroxyalkyl, hydroxyalkoxyalkyl, alkoxyhydroxyalkyl, alkoxycarbonylalkyl, dioxanylylalkyl and a polyalkoxyalkyl residue each of which is unsubstituted or substituted by a hydroxy residue in the alkyl moiety.

5. The method according to claim 1, wherein said aromatic nitroso compound is a compound of formula I:

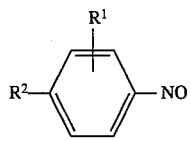 (I)

wherein $R^1$ is selected from the group consisting of hydrogen; hydroxy; an alkyl which is unsubstituted or substituted by hydroxy, COOH, $PO_3H_2$, or $SO_3H$; alkoxy; alkylthio; aryloxy; arylthio; halogen; and an amino which is unsubstituted or substituted at least once by an alkyl which is unsubstituted or substituted by hydroxy, $PO_3H_2$, dialkylphosphinyl, $SO_3H$ or $CO_2H$;

$R^2$ is selected from the group consisting of a hydroxy group, an alkoxy group, an aryloxy group, an arylthio group, an alkylthio group, an amino group which is unsubstituted or substituted at least once by alkyl, $PO_3H_2$, $SO_3H$, $CO_2H$, or an ammonium, alkali or alkaline earth salt form of $PO_3H_2$, $SO_3H$, or $CO_2H$, and an amino group $NR^3R^4$, wherein said alkoxy, aryloxy, arylthio or alkylthio groups are unsubstituted or the alkyl residue is substituted by a hydroxy group, $R^1$ is in an ortho position in relation to $NR^3R^4$, and $R^3$ or $R^4$ together with $R^1$ form an alkylene residue.

6. The method according to claim 1, wherein said aromatic nitroso compound is a compound of formula II:

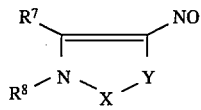 (II)

wherein

X-Y is selected from the group consisting of $NR^5$—CO and N=$CR^6$, $R^5$ is selected from the group consisting of hydrogen, an alkyl group which is unsubstituted or substituted by a residue selected from the group consisting of hydroxy, carboxy, $SO_3H$, $PO_3H_2$, and dialkylphosphinyl, $R^6$ is selected from the group consisting of hydrogen, alkyl, alkenyl, alkoxy, alkylthio, aryl, arylthio, aralkyl, dialkylphosphinyl, and an amino which is unsubstituted or substituted by one or two alkyl residues which in turn are unsubstituted or substituted by at least one hydroxy, carboxy, or alkoxycarbonyl residues, wherein said alkyl, alkenyl, alkoxy, alkylthio, aryl, arylthio, and aralkyl groups are unsubstituted or substituted by hydroxy, carboxy, $SO_3H$, $PO_3H_2$, a salt of $SO_3H$, a salt of $PO_3H_2$, or alkoxycarbonyl, $R^7$ is selected from the group consisting of alkyl, thioalkyl, aralkyl, an amino group which is unsubstituted or substituted by one or two alkyl groups which in turn are unsubstituted or substituted by hydroxy, carboxy, $SO_3H$, dialkylphosphinyl or $PO_3H_2$, wherein said alkyl, thioalkyl and aralkyl are unsubstituted or substituted by hydroxy, carboxy, $SO_3H$ or $PO_3H_2$, wherein at least one of $R^6$ and $R^7$ is an amino group and $R^8$ is selected from the group consisting of an alkyl or aralkyl group which is unsubstituted or substituted by hydroxy, carboxy, $SO_3H$ or $PO_3H_2$, as well as corresponding tautomeric forms and their salts.

7. The method according to claim 6, wherein $R^6$ is an amino substituted by 2 alkyl residues, and wherein these residues are linked to form a ring which apart from the N atom of the amino group, said ring is uninterrupted or interrupted by oxygen, sulphur, a further nitrogen atom, or an amino group which is unsubstituted or substituted by one or two groups selected from the group consisting of an alkyl group, an alkoxy group, an aralkoxycarbonyl group, $H_2N$—CO, an aralkyl group, an arylcarbamoyl group, hydrogen, carboxy, alkoxycarbonyl, carboxamido and halogen.

8. The method according to claim 1, wherein said aromatic nitroso compound is a compound of formula II:

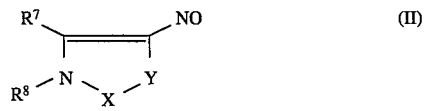 (II)

wherein

X-Y is selected from the group consisting of $NR^5$—CO and N=$CR^6$, $R^5$ is selected from the group consisting of hydrogen, an alkyl group which is unsubstituted or substituted by a residue selected from the group consisting of hydroxy, carboxy, $SO_3H$, $PO_3H_2$, and dialkylphosphinyl, $R^6$ is selected from the group consisting of hydrogen, alkyl, alkenyl, alkoxy, alkylthio, aryl, arylthio, aralkyl, dialkylphosphinyl, and an amino which is unsubstituted or substituted by one or two alkyl residues which in turn are unsubstituted or substituted by at least one hydroxy, carboxy, or alkoxycarbonyl residues, wherein said alkyl, alkenyl, alkoxy, alkylthio, aryl, arylthio, and aralkyl groups are unsubstituted or substituted by hydroxy, carboxy, $SO_3H$, $PO_3H_2$, a salt of $SO_3H$, a salt of $PO_3H_2$, or alkoxycarbonyl, $R^7$ and $R^8$ form a saturated or unsaturated chain with 3 or 4 members selected from the group consisting of nitrogen atoms, carbon atoms and sulphur atoms, wherein said carbon atoms are unsubstituted or substituted by alkyl, alkoxy, alkylthio, hydroxy, aralkyl, aryl, carboxy, carboxamido, alkoxycarbonyl, cyano, halogen, an amino which is unsubstituted or substituted by one or two alkyl residues which are unsubstituted or substituted by at least one hydroxy, carboxy or alkoxycarbonyl residue and wherein any nitrogen atoms which are not bound via a double bond are substituted by alkyl, aralkyl or dialkylphosphinyl; wherein two adjacent chain substituents form an alkylene group which in turn is unsubstituted or substituted by aryl or is anellated, as well as corresponding tautomeric forms and their salts.

9. The method according to claim 1, wherein said non-oxidative chromogenic detection reagent is a coupling reagent for imino compounds.

10. The method according to claim 9, wherein said coupling reagent is selected from the group consisting of a phenol, naphthol, aniline and naphthylamine derivative.

11. The method according to claim 9, wherein said coupling reagent is selected from the group consisting of 2,4,6-tribromo-3-hydroxybenzoic acid, 2,4-dibromo-1-naphthol and 1-naphthol-4-sulfonic acid.

12. The method according to claim 1, wherein the imino compound is detected by oxidation of a leuco dye to a dye.

13. The method according to claim 12, wherein said leuco dye is selected from the group consisting of diarylimidazoles, triarylimidazoles and naphthylamines.

14. A method for the colorimetric determination of an analyte, comprising, enzymatically oxidizing an analyte with an oxidoreductase in the presence of a direct electron acceptor, wherein said direct electron acceptor is an electron-rich aromatic nitroso compound, wherein the electron-rich aromatic nitroso compound is reduced in the presence of a POO-dependent dehydrogenase to a colored imino compound without further enzymatic reduction to an aromatic amine with concomitant oxidation of the analyte, and measuring any color formation of the imino compound, wherein said electron rich aromatic nitroso compound is a compound of the general formula XIII:

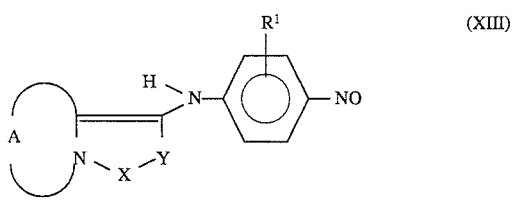
(XIII)

wherein $R^1$ is selected from the group consisting of hydrogen, hydroxy, halogen, alkoxy, alkylthio, aryloxy, arylthiol, an alkyl which is unsubstituted or substituted by hydroxy, carboxy, $PO_3H_2$ or $SO_3H$, an amino which is unsubstituted or substituted at least once by an alkyl which in turn is unsubstituted or substituted by hydroxy, $PO_3H_2$, dialkylphosphinyl, $SO_3H$ or carboxy, X-Y is selected from the group consisting of $NR^5$—CO and $N$=$CR^6$, $R^5$ is selected from the group consisting of hydrogen, an alkyl which is unsubstituted or substituted by hydroxy, carboxy, $SO_3H$, $PO_3H_2$, and dialkylphosphinyl, $R^6$ is selected from the group consisting of hydrogen, alkyl, alkenyl, alkoxy, alkylthio, aryl, arylthio, aralkyl, and an amino which is unsubstituted or substituted by one or two alkyl residues which are in turn unsubstituted or substituted with at least one hydroxy, carboxy, or alkoxycarbonyl residue, wherein said alkyl, alkenyl, alkoxy, alkylthio, aryl, arylthio, and aralkyl are unsubstituted or substituted by hydroxy, carboxy, $SO_3H$, $PO_3H_2$, a salt of $SO_3H$, a salt of $PO_3H_2$, or alkoxycarbonyl, A is a saturated or unsaturated chain consisting of three members selected from the group consisting of nitrogen, sulphur and carbon, wherein the carbon atoms are unsubstituted or substituted by alkyl, alkoxy, alkylthio, hydroxy, aralkyl, aryl, carboxy, carboxamido, alkoxycarbonyl, cyano, halogen, an amino which is unsubstituted or substituted by one or two alkyl residues which in turn are substituted or unsubstituted with at least one hydroxy, carboxy or alkoxycarbonyl residue and wherein any nitrogen atoms that are not bound via a double bond are substituted by hydrogen, aralkyl, or an alkyl which is unsubstituted or substituted by $SO_3H_2$, $PO_3H_2$, carboxy or dialkylphosphinyl, as well as corresponding tautomeric forms and their salts, which react enzymatically to form a colored quinone diimine as a measure of the amount of the analyte.

15. The method according to claim 14, wherein $R^6$ is an amino substituted by two alkyl residues, wherein said residues are linked to form a ring, and wherein apart from the N atom of the amino group said ring is uninterrupted or interrupted by oxygen; sulphur; a further nitrogen atom; an amino which is unsubstituted or substituted by one or two groups selected from the group consisting of acyl, alkoxy, aralkoxycarbonyl, $H_2N$—CO, alkyl, aralkyl, and arylcarbamoyl; carboxy; alkoxycarbonyl; carboxamido; and halogen.

16. The method according to claim 14, wherein A forms an imidazole, triazole, benzimidazole, thiazole or dihydroimidazole ring with an adjacent heterocycle.

17. The method according to claim 14, wherein the aromatic nitroso compound is in a concentration of more than 10–13 mol/l.

18. The method according to claim 1, wherein said aromatic nitrosoaniline compound is a compound of the general formula XIII:

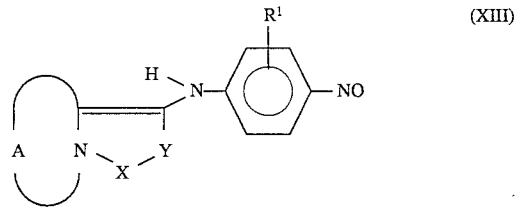
(XIII)

wherein $R^1$ is selected from the group consisting of hydrogen, hydroxy, halogen, alkoxy, alkylthio, aryloxy, arylthiol, an alkyl which is unsubstituted or substituted by hydroxy, carboxy, $PO_3H_2$ or $SO_3H$, an amino which is unsubstituted or substituted at least once by an alkyl which in turn is unsubstituted or substituted by hydroxy, $PO_3H_2$, dialkylphosphinyl, $SO_3H$ or carboxy, X-Y is selected from the group consisting of $NR^5$—CO and $N$=$CR^6$, $R^5$ is selected from the group consisting of hydrogen, an alkyl which is unsubstituted or substituted by hydroxy, carboxy, $SO_3H$, $PO_3H_2$, and dialkylphosphinyl, $R^6$ is selected from the group consisting of hydrogen, alkyl, alkenyl, alkoxy, alkylthio, aryl, arylthio, aralkyl, and an amino which is unsubstituted or substituted by one or two alkyl residues which are in turn unsubstituted or substituted with at least one hydroxy, carboxy, or alkoxycarbonyl residue; wherein said alkyl, alkenyl, alkoxy, alkylthio, aryl, arylthio, and aralkyl are unsubstituted or substituted by hydroxy, carboxy, $SO_3H$, $PO_3H_2$, a salt of $SO_3H$, a salt of $PO_3H_2$, or alkoxycarbonyl, A is a saturated or unsaturated chain consisting of three members selected from the group consisting of nitrogen, sulphur and carbon, wherein the carbon atoms are unsubstituted or substituted by alkyl, alkoxy, alkylthio, hydroxy, aralkyl, aryl, carboxy, carboxamido, alkoxycarbonyl, cyano, halogen, an amino which is unsubstituted or substituted by one or two alkyl residues which in turn are substituted or unsubstituted with at least one hydroxy, carboxy or alkoxycarbonyl residue and wherein any nitrogen atoms that are not bound via a double bond are substituted by hydrogen, aralkyl, or an alkyl which is unsubstituted or substituted by $SO_3H_2$, $PO_3H_2$, carboxy or dialkylphosphinyl, wherein two adjacent chain substituents form an alkylene group which is unsubstituted, substituted by aryl, or is anellated, as well as corresponding tautomeric forms and their salts which react enzymatically to form a colored quinone diimine as a measure of the amount of the analyte.

19. The method according to claim 1, wherein said PQQ-dependent dehydrogenase is glucose dye oxidoreductase and said analyte to be determined is glucose.

20. A reagent for the colorimetric determination of an analyte by enzymatic oxidation of said analyte, comprising PQQ-dependent dehydrogenase, an electron-rich aromatic nitroso compound, and a color-forming, non-oxidative detection reagent for imino compounds.

21. The reagent according to claim 20, wherein said nitroso compound is a compound of the general formula I,

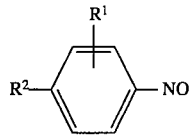

wherein $R^1$ is selected from the group consisting of hydrogen; hydroxy; an alkyl which is unsubstituted or substituted by hydroxy, COOH, $PO_3H_2$, or $SO_3H$; alkoxy; alkylthio; aryloxy; arylthio; halogen; and an amino which is unsubstituted or substituted at least once by an alkyl which is unsubstituted or substituted by hydroxy, $PO_3H_2$, dialkylphosphinyl, $SO_3H$ or $CO_2H$;

$R^2$ is selected from the group consisting of a hydroxy group, an alkoxy group, an aryloxy group, an arylthio group, an alkylthio group, an amino group which is unsubstituted or substituted at least once by alkyl, $PO_3H_2$, $SO_3H$, $CO_2H$, or an ammonium, alkali or alkaline earth salt form of $PO_3H_2$, $SO_3H$, or $CO_2H$; and an amino group $NR^3R^4$, wherein said alkoxy, aryloxy, arylthio or alkylthio groups are unsubstituted or the alkyl residue is substituted by a hydroxy group, and $R^3$ and $R^4$ are individually selected from the group consisting of hydrogen, an aryl group, an alkyl group, an alkoxy group, a hydroxyalkoxy group, a polyalkoxy group which is unsubstituted or substituted by hydroxy, $PO_3H_2$, $SO_3H$, COOH, a salt form of $PO_3H_2$, a salt form of $SO_3H$, or a salt form of COOH, and an amino group which is unsubstituted or substituted at least once by an alkyl group, wherein said aryl group and said alkyl group are unsubstituted or substituted by a hydroxy.

22. The reagent according to claim 20, wherein said nitroso compound is a compound of the general formula I,

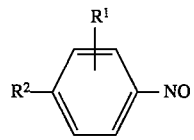

wherein $R^1$ is selected from the group consisting of hydrogen; hydroxy; an alkyl which is unsubstituted or substituted by hydroxy, COOH, $PO_3H_2$ or $SO_3H$; alkoxy; alkylthio; aryloxy; arylthio; halogen; and an amino which is unsubstituted or substituted at least once by an alkyl which is unsubstituted or substituted by hydroxy, $PO_3H_2$, dialkylphosphinyl, $SO_3H$ or $CO_2H$;

$R^2$ is selected from the group consisting of a hydroxy group, an alkoxy group, an aryloxy group, an arylthio group, an alkylthio group, an amino group which is unsubstituted or substituted at least once by alkyl, $PO_3H_2$, $SO_3H$, $CO_2H$, an ammonium, alkali or alkaline earth salt form of $PO_3H_2$, $SO_3H$ or $CO_2H$, and an amino group $NR^3R^4$, wherein said alkoxy, aryloxy, arylthio or alkylthio groups are unsubstituted or the alkyl residue is substituted by a hydroxy group, and $R^3$ and $R^4$ form an alkylene residue which is uninterrupted or interrupted by oxygen, sulphur or nitrogen, wherein said nitrogen is substituted by a residue selected from the group consisting of an alkyl, hydroxyalkyl, hydroxyalkoxyalkyl, alkoxyhydroxyalkyl, alkoxycarbonylalkyl, dioxanylylalkyl and a polyalkoxyalkyl residue each of which is unsubstituted or substituted by a hydroxy residue in the alkyl moiety.

23. The reagent according to claim 20, wherein said nitroso compound is a compound of the general formula I,

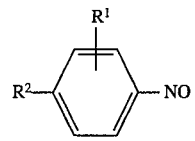

wherein $R^1$ is selected from the group consisting of hydrogen; hydroxy; an alkyl which is unsubstituted or substituted by hydroxy, COOH, $PO_3H_2$ or $SO_3H$; alkoxy; alkylthio; aryloxy; arylthio; halogen; and an amino which is unsubstituted or substituted at least once by an alkyl which is unsubstituted or substituted by hydroxy, $PO_3H_2$, dialkylphosphinyl, $SO_3H$ or $CO_2H$;

$R^2$ is selected from the group consisting of a hydroxy group, an alkoxy group, an aryloxy group, an arylthio group, an alkylthio group, an amino group which is unsubstituted or substituted at least once by alkyl, $PO_3H_2$, $SO_3H$, $CO_2H$, or an ammonium, alkali or alkaline earth salt form of $PO_3H_2$, $SO_3H$ or $CO_2H$, and an amino group $NR^3R^4$, wherein said alkoxy, aryloxy, arylthio or alkylthio groups are unsubstituted or the alkyl residue is substituted by a hydroxy group, $R^1$ is in an ortho position in relation to $NR^3R^4$ and $R^3$ or $R^4$ together with $R^1$ form an alkylene residue.

24. The reagent according to claim 20, wherein said nitroso compound is a compound of the general formula II,

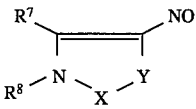

wherein

X-Y is selected from the group consisting of $NR^5$—CO and $N=CR^6$, $R^5$ is selected from the group consisting of hydrogen, an alkyl group which is unsubstituted or substituted by a residue selected from the group consisting of hydroxy, carboxy, $SO_3H$, $PO_3H_2$, and dialkylphosphinyl, $R^6$ is selected from the group consisting of hydrogen, alkyl, alkenyl, alkoxy, alkylthio, aryl, arylthio, aralkyl, dialkylphosphinyl, and an amino which is unsubstituted or substituted by one or two alkyl residues which in turn are unsubstituted or substituted by at least one hydroxy, carboxy, or alkoxycarbonyl residues, wherein said alkyl, alkenyl, alkoxy, alkylthio, aryl, arylthio, and aralkyl groups are unsubstituted or substituted by hydroxy, carboxy, $SO_3H$, $PO_3H_2$, a salt of $SO_3H$, a salt of $PO_3H_2$, or alkoxycarbonyl, $R^7$ is selected from the group consisting of alkyl, thioalkyl, aralkyl, an amino group which is unsubstituted or substituted by one or two alkyl groups which in turn are unsubstituted or substituted by hydroxy, carboxy, $SO_3H$, dialkylphosphinyl or $PO_3H_2$, wherein said alkyl, thioalkyl and aralkyl are unsubstituted or substituted by hydroxy, carboxy, SO₃H or PO₃H₂, wherein at least one of $R^6$ and $R^7$ is an amino group and $R^8$ is selected from the group consisting of an alkyl or aralkyl group which is unsubstituted or substituted by hydroxy, carboxy, SO₃H or PO₃H₂, as well as corresponding tautomeric forms and their salts.

25. The reagent according to claim 24, wherein $R^6$ is an amino substituted by 2 alkyl residues, and wherein these residues are linked to form a ring which apart from the N atom of the amino group, said ring is uninterrupted or interrupted by oxygen, sulphur, a further nitrogen atom, or an amino group which is unsubstituted or substituted by one or two groups selected from the group consisting of an alkyl group, an alkoxy group, an aralkoxycarbonyl group, H₂N—CO, an aralkyl group, an arylcarbamoyl group, hydrogen, carboxy, alkoxycarbonyl, carboxamido and halogen.

26. The reagent according to claim 20, wherein said aromatic nitroso compound is a compound of formula II:

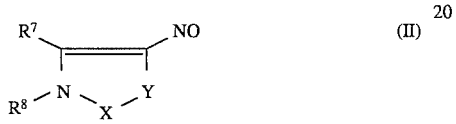

(II)

wherein

X-Y is selected from the group consisting of $NR^5$—CO and $N=CR^6$, $R^5$ is selected from the group consisting of hydrogen, an alkyl group which is unsubstituted or substituted by a residue selected from the group consisting of hydroxy, carboxy, SO₃H, PO₃H₂, and dialkylphosphinyl, $R^6$ is selected from the group consisting of hydrogen, alkyl, alkenyl, alkoxy, alkylthio, aryl, arylthio, aralkyl, dialkylphosphinyl, and an amino which is unsubstituted or substituted by one or two alkyl residues which in turn are unsubstituted or substituted by at least one hydroxy, carboxy, or alkoxycarbonyl residues, wherein said alkyl, alkenyl, alkoxy, alkylthio, aryl, arylthio, and aralkyl groups are unsubstituted or substituted by hydroxy, carboxy, SO₃H, PO₃H₂, a salt of SO₃H, a salt of PO₃H₂, or alkoxycarbonyl, $R^7$ and $R^8$ form a saturated or unsaturated chain with 3 or 4 members selected from the group consisting of nitrogen atoms, carbon atoms and sulphur atoms, wherein said carbon atoms are unsubstituted or substituted by alkyl, alkoxy, alkylthio, hydroxy, aralkyl, aryl, carboxy, carboxamido, alkoxycarbonyl, cyano, halogen, an amino which is unsubstituted or substituted by one or two alkyl residues which are unsubstituted or substituted by at least one hydroxy, carboxy or alkoxycarbonyl residue and wherein any nitrogen atoms which are not bound via a double bond are substituted by alkyl, aralkyl or dialkylphosphinyl; wherein two adjacent chain substituents form an alkylene group which in turn is unsubstituted or substituted by aryl or is anellated, as well as corresponding tautomeric forms and their salts.

27. A reagent according to claim 20, wherein said non-oxidative detection reagent for imino compounds is a chromogenic coupling reagent for imino compounds or a leuco dye.

28. A test carrier comprising a reagent according to claim 20.

29. A reagent for the colorimetric determination of an analyte by enzymatic oxidation of the analyte, comprising a PQQ-dependent dehydrogenase and an electron-rich aromatic nitroso compound, wherein the electron-rich aromatic nitroso compound is a nitrosoaniline compound of formula XIII,

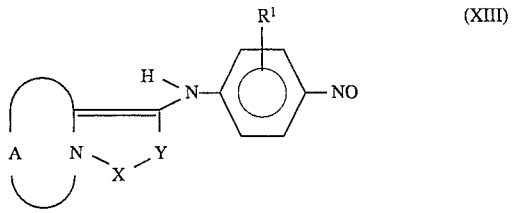

(XIII)

wherein $R^1$ is selected from the group consisting of hydrogen, hydroxy, halogen, alkoxy, alkylthio, aryloxy, arylthiol, an alkyl which is unsubstituted or substituted by hydroxy, carboxy, PO₃H₂ or SO₃H, an amino which is unsubstituted or substituted at least once by an alkyl which in turn is unsubstituted or substituted by hydroxy, PO₃H₂, dialkylphosphinyl, SO₃H or carboxy, X-Y is selected from the group consisting of $NR^5$—CO and $N=CR^6$, $R^5$ is selected from the group consisting of hydrogen, an alkyl which is unsubstituted or substituted by hydroxy, carboxy, SO₃H, PO₃H₂, and dialkylphosphinyl, $R^6$ is selected from the group consisting of hydrogen, alkyl, alkenyl, alkoxy, alkylthio, aryl, arylthio, aralkyl, and an amino which is unsubstituted or substituted by one or two alkyl residues which are in turn unsubstituted or substituted with at least one hydroxy, carboxy, or alkoxycarbonyl residue, wherein said alkyl, alkenyl, alkoxy, alkylthio, aryl, arylthio, and aralkyl are unsubstituted or substituted by hydroxy, carboxy, SO₃H, PO₃H₂, a salt of SO₃H, a salt of PO₃H₂, or alkoxycarbonyl, A is a saturated or unsaturated chain consisting of three members selected from the group consisting of nitrogen, sulphur and carbon, wherein the carbon atoms are unsubstituted or substituted by alkyl, alkoxy, alkylthio, hydroxy, aralkyl, aryl, carboxy, carboxamido, alkoxycarbonyl, cyano, halogen, an amino which is unsubstituted or substituted by one or two alkyl residues which in turn are substituted or unsubstituted with at least one hydroxy, carboxy or alkoxycarbonyl residue and wherein any nitrogen atoms that are not bound via a double bond are substituted by hydrogen, aralkyl, or an alkyl which is unsubstituted or substituted by SO₃H₂, PO₃H₂, carboxy or dialkylphosphinyl, as well as corresponding tautomeric forms and their salts.

30. The reagent according to claim 29, wherein $R^6$ is an amino substituted by two alkyl residues, wherein said residues are linked to form a ring, and wherein apart from the N atom of the amino group said ring is uninterrupted or interrupted by oxygen; sulphur; a further nitrogen atom; an amino which is unsubstituted or substituted by one or two groups selected from the group consisting of acyl, alkoxy, aralkoxycarbonyl, H₂N—CO, alkyl, aralkyl, and arylcarbamoyl; carboxy; alkoxycarbonyl; carboxamido; and halogen.

31. The reagent according to claim 29, wherein A forms an imidazole, triazole, benzimidazole, thiazole or dihydroimidazole ring with an adjacent heterocycle.

32. A reagent for the colorimetric determination of an analyte by enzymatic oxidation of the analyte, comprising a PQQ-dependent dehydrogenase and an electron-rich aromatic nitroso compound, wherein the electron-rich aromatic nitroso compound is a nitrosoaniline compound of formula XIII:

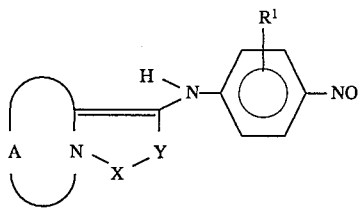

(XIII)

wherein $R^1$ is selected from the group consisting of hydrogen, hydroxy, halogen, alkoxy, alkylthio, aryloxy, arylthiol, an alkyl which is unsubstituted or substituted by hydroxy, carboxy, $PO_3H_2$ or $SO_3H$, an amino which is unsubstituted or substituted at least once by an alkyl which in turn is unsubstituted or substituted by hydroxy, $PO_3H_2$, dialkylphosphinyl, $SO_3H$ or carboxy, X-Y is selected from the group consisting of $NR^5$—CO and $N$=$CR^6$, $R^5$ is selected from the group consisting of hydrogen, an alkyl which is unsubstituted or substituted by hydroxy, carboxy, $SO_3H$, $PO_3H_2$, and dialkylphosphinyl, $R^6$ is selected from the group consisting of hydrogen, alkyl, alkenyl, alkoxy, alkylthio, aryl, arylthio, aralkyl, and an amino which is unsubstituted or substituted by one or two alkyl residues which are in turn unsubstituted or substituted with at least one hydroxy, carboxy, or alkoxycarbonyl residue; wherein said alkyl, alkenyl, alkoxy, alkylthio, aryl, arylthio, and aralkyl are unsubstituted or substituted by hydroxy, carboxy, $SO_3H$, $PO_3H_2$, a salt of $SO_3H$, a salt of $PO_3H_2$, or alkoxycarbonyl, A is a saturated or unsaturated chain consisting of three members selected from the group consisting of nitrogen, sulphur and carbon, wherein the carbon atoms are unsubstituted or substituted by alkyl, alkoxy, alkylthio, hydroxy, aralkyl, aryl, carboxy, carboxamido, alkoxycarbonyl, cyano, halogen, an amino which is unsubstituted or substituted by one or two alkyl residues which in turn are substituted or unsubstituted with at least one hydroxy, carboxy or alkoxycarbonyl residue and wherein any nitrogen atoms that are not bound via a double bond are substituted by hydrogen, aralkyl, or an alkyl which is unsubstituted or substituted by $SO_3H_2$, $PO_3H_2$, carboxy or dialkylphosphinyl; wherein two adjacent chain substituents form an alkylene group which is unsubstituted or substituted by aryl or is anellated, as well as corresponding tautomeric forms and their salts.

* * * * *